United States Patent
Krishna et al.

(10) Patent No.: US 8,852,235 B2
(45) Date of Patent: Oct. 7, 2014

(54) POSTERIORLY INSERTED ARTIFICIAL DISC AND AN ARTIFICIAL FACET JOINT

(75) Inventors: Manoj Krishna, Yarm (GB); Tai Friesen, Ingleby (GB)

(73) Assignee: Spinadyne, Inc., Naples, FL (US)

( * ) Notice: Subject to any disclaimer, the term of this patent is extended or adjusted under 35 U.S.C. 154(b) by 0 days.

(21) Appl. No.: 11/852,020

(22) Filed: Sep. 11, 2007

(65) Prior Publication Data

US 2008/0033562 A1 Feb. 7, 2008

Related U.S. Application Data

(62) Division of application No. 10/970,091, filed on Oct. 21, 2004, now abandoned.

(30) Foreign Application Priority Data

Oct. 15, 2004 (GB) .................................. 0422963.9

(51) Int. Cl.
*A61B 17/70* (2006.01)

(52) U.S. Cl.
USPC ........... 606/257; 606/246; 606/259; 606/261; 606/264

(58) Field of Classification Search
USPC ............. 606/57, 58, 246, 247, 254–261, 282; 623/17.11–17.16; 403/119, 161, 162
See application file for complete search history.

(56) References Cited

U.S. PATENT DOCUMENTS

| 4,349,921 A | 9/1982 | Kuntz |
| 4,368,997 A * | 1/1983 | Shemtov ........................ 403/59 |
| 4,488,542 A * | 12/1984 | Helland .......................... 606/59 |
| 5,034,011 A * | 7/1991 | Howland ....................... 606/256 |
| 5,122,140 A * | 6/1992 | Asche et al. .................... 606/55 |
| 5,258,031 A | 11/1993 | Salib et al. |
| 5,314,477 A | 5/1994 | Marnay |
| 5,375,823 A | 12/1994 | Navas |
| 5,401,269 A | 3/1995 | Buttner-Janz et al. |
| 5,423,816 A | 6/1995 | Lin |
| 5,425,773 A | 6/1995 | Boyd et al. |
| 5,480,401 A | 1/1996 | Navas |
| 5,507,816 A | 4/1996 | Bullivant |
| 5,556,431 A | 9/1996 | Buttner-Janz |
| 5,562,736 A | 10/1996 | Ray et al. |
| 5,562,737 A | 10/1996 | Graf |
| 5,562,738 A | 10/1996 | Boyd et al. |

(Continued)

FOREIGN PATENT DOCUMENTS

FR 2728158 A1 * 6/1996

*Primary Examiner* — Nicholas Woodall
(74) *Attorney, Agent, or Firm* — Christopher & Weisberg, P.A.

(57) ABSTRACT

Lumbar disc and facet joint replacement prosthesis are provided. The lumbar disc prosthesis includes first member having a vertebral disc contact surface and a recessed portion on an opposing surface thereof and a second member having a vertebral disc contact surface and a protruding portion on an opposing surface thereof. The protruding portion of the second member engages the recessed portion of the first member in use. The first and second members are provided with at least a middle section and two end sections. The recessed and protruding portions are provided in the middle section of the respective members and each end section has a narrowing taper. The facet joint prosthesis includes a first member for attachment to a first posterior lumbar disc and a second member for attachment to a second posterior lumbar disc. At least a part of the first member is telescopically mounted in at least a part of the second member.

8 Claims, 30 Drawing Sheets

(56) References Cited

U.S. PATENT DOCUMENTS

| | | |
|---|---|---|
| 5,672,175 A | 9/1997 | Martin |
| 5,676,701 A | 10/1997 | Yuan et al. |
| 5,733,284 A | 3/1998 | Martin |
| 5,755,796 A * | 5/1998 | Ibo et al. .................... 623/17.16 |
| 5,782,832 A | 7/1998 | Larsen et al. |
| 5,888,226 A | 3/1999 | Rogozinski |
| 5,899,941 A | 5/1999 | Nishijima et al. |
| 6,019,792 A | 2/2000 | Cauthen |
| 6,039,763 A | 3/2000 | Shelokov |
| 6,063,121 A | 5/2000 | Xavier et al. |
| 6,113,637 A | 9/2000 | Gill et al. |
| 6,146,421 A | 11/2000 | Gordon et al. |
| 6,228,118 B1 | 5/2001 | Gordon |
| 6,241,730 B1 * | 6/2001 | Alby ............................ 606/256 |
| 6,267,764 B1 * | 7/2001 | Elberg .......................... 606/255 |
| 6,283,968 B1 | 9/2001 | Mehdizadeh |
| 6,296,644 B1 * | 10/2001 | Saurat et al. ................. 606/256 |
| 6,306,136 B1 * | 10/2001 | Baccelli ....................... 606/279 |
| 6,368,350 B1 | 4/2002 | Erickson et al. |
| 6,375,683 B1 * | 4/2002 | Crozet et al. ............... 623/17.15 |
| 6,402,750 B1 | 6/2002 | Atkinson et al. |
| 6,436,098 B1 | 8/2002 | Michelson |
| 6,440,168 B1 | 8/2002 | Cauthen |
| 6,520,996 B1 | 2/2003 | Manasas et al. |
| 6,527,804 B1 | 3/2003 | Gauchet et al. |
| 6,540,785 B1 | 4/2003 | Gill et al. |
| 6,579,320 B1 | 6/2003 | Gauchet et al. |
| 6,620,164 B2 * | 9/2003 | Ueyama et al. .............. 606/261 |
| 6,626,904 B1 | 9/2003 | Jammet et al. |
| 6,626,905 B1 | 9/2003 | Schmiel et al. |
| 6,669,729 B2 | 12/2003 | Chin |
| 6,679,915 B1 | 1/2004 | Cauthen |
| 6,682,562 B2 | 1/2004 | Viart et al. |
| 6,706,068 B2 | 3/2004 | Ferree |
| 6,726,720 B2 | 4/2004 | Ross et al. |
| 6,733,532 B1 | 5/2004 | Gauchet et al. |
| 6,770,095 B2 | 8/2004 | Grinberg et al. |
| 6,802,867 B2 | 10/2004 | Manasas et al. |
| 6,830,570 B1 | 12/2004 | Frey et al. |
| 6,835,205 B2 | 12/2004 | Atkinson et al. |
| 6,835,207 B2 | 12/2004 | Zacouto et al. |
| 6,852,128 B2 | 2/2005 | Lange |
| 6,878,167 B2 | 4/2005 | Ferree |
| 6,936,070 B1 | 8/2005 | Muhanna |
| 6,936,071 B1 | 8/2005 | Marnay et al. |
| 6,945,974 B2 | 9/2005 | Dalton |
| 6,972,037 B2 | 12/2005 | Zubok et al. |
| 6,974,478 B2 | 12/2005 | Reiley et al. |
| 6,986,771 B2 | 1/2006 | Paul et al. |
| 6,986,789 B2 | 1/2006 | Schultz et al. |
| 6,989,011 B2 | 1/2006 | Paul et al. |
| 6,994,727 B2 | 2/2006 | Khandkar et al. |
| 7,001,432 B2 | 2/2006 | Keller et al. |
| 7,014,633 B2 | 3/2006 | Cragg |
| 7,025,787 B2 | 4/2006 | Bryan et al. |
| 7,029,475 B2 | 4/2006 | Panjabi |
| 7,033,392 B2 | 4/2006 | Schmiel et al. |
| 7,037,340 B2 | 5/2006 | Gau |
| 7,041,136 B2 | 5/2006 | Goble et al. |
| 7,048,764 B2 | 5/2006 | Ferree |
| 7,052,515 B2 | 5/2006 | Simonson |
| 7,074,237 B2 | 7/2006 | Goble et al. |
| 7,074,238 B2 | 7/2006 | Stinson et al. |
| 7,083,622 B2 | 8/2006 | Simonson |
| 7,083,649 B2 | 8/2006 | Zucherman et al. |
| 7,087,084 B2 | 8/2006 | Reiley |
| 7,090,698 B2 | 8/2006 | Goble et al. |
| 7,195,643 B2 | 3/2007 | Jackson |
| 7,202,992 B2 | 4/2007 | Kawai |
| 7,204,852 B2 | 4/2007 | Marnay et al. |
| 7,207,992 B2 | 4/2007 | Ritland |
| 7,270,681 B2 | 9/2007 | Cauthen |
| 7,276,082 B2 | 10/2007 | Zdeblick et al. |
| 7,282,065 B2 | 10/2007 | Kirschman |
| 7,291,150 B2 | 11/2007 | Graf |
| 7,326,210 B2 | 2/2008 | Jahng et al. |
| 7,329,258 B2 | 2/2008 | Studer |
| 7,331,995 B2 | 2/2008 | Eisermann et al. |
| 7,503,934 B2 | 3/2009 | Eisermann et al. |
| 7,556,651 B2 | 7/2009 | Humphreys et al. |
| 2003/0040802 A1 | 2/2003 | Errico et al. |
| 2003/0208273 A1 | 11/2003 | Eisermann et al. |
| 2004/0010316 A1 | 1/2004 | William et al. |
| 2004/0138749 A1 | 7/2004 | Zucherman et al. |
| 2004/0143332 A1 | 7/2004 | Keueger et al. |
| 2004/0158254 A1 | 8/2004 | Eisermann |
| 2004/0158328 A1 | 8/2004 | Eisermann |
| 2004/0176772 A1 | 9/2004 | Zubok et al. |
| 2004/0176845 A1 | 9/2004 | Zubok et al. |
| 2004/0176853 A1 | 9/2004 | Sennett et al. |
| 2004/0181285 A1 | 9/2004 | Simonson |
| 2004/0236329 A1 | 11/2004 | Panjabi |
| 2005/0043800 A1 | 2/2005 | Paul et al. |
| 2005/0049592 A1 | 3/2005 | Keith et al. |
| 2005/0049708 A1 | 3/2005 | Atkinson et al. |
| 2005/0149188 A1 | 7/2005 | Cook et al. |
| 2005/0154461 A1 | 7/2005 | Humphreys et al. |
| 2005/0154464 A1 | 7/2005 | Humphreys et al. |
| 2005/0154466 A1 | 7/2005 | Humphreys et al. |
| 2005/0154467 A1 | 7/2005 | Peterman et al. |
| 2005/0171543 A1 | 8/2005 | Timm et al. |
| 2005/0171610 A1 | 8/2005 | Humphreys et al. |
| 2005/0177156 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0222569 A1 | 10/2005 | Panjabi |
| 2005/0228497 A1 | 10/2005 | Ferree et al. |
| 2005/0240265 A1 | 10/2005 | Kuiper et al. |
| 2005/0245930 A1 | 11/2005 | Timm et al. |
| 2005/0256578 A1 | 11/2005 | Blatt et al. |
| 2005/0261682 A1 | 11/2005 | Ferree |
| 2006/0036240 A1 | 2/2006 | Colleran et al. |
| 2006/0036326 A1 | 2/2006 | Baumgartner et al. |
| 2006/0069438 A1 | 3/2006 | Zucherman et al. |
| 2006/0069441 A1 | 3/2006 | Zucherman et al. |
| 2006/0084994 A1 | 4/2006 | Atkinson et al. |
| 2006/0089717 A1 | 4/2006 | Krishna et al. |
| 2006/0149229 A1 * | 7/2006 | Kwak et al. .................... 606/61 |
| 2006/0184171 A1 | 8/2006 | Biedermann et al. |
| 2006/0189984 A1 | 8/2006 | Fallin et al. |
| 2006/0247637 A1 * | 11/2006 | Colleran et al. ................ 606/61 |
| 2006/0247779 A1 | 11/2006 | Gordon et al. |
| 2006/0271051 A1 * | 11/2006 | Berrevoets et al. ............. 606/61 |
| 2006/0285916 A1 * | 12/2006 | Lu et al. ........................ 403/119 |
| 2007/0179616 A1 | 8/2007 | Braddock, Jr. et al. |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0270862 A1 | 11/2007 | Yu et al. |
| 2012/0136445 A1 | 5/2012 | Krishna et al. |

* cited by examiner

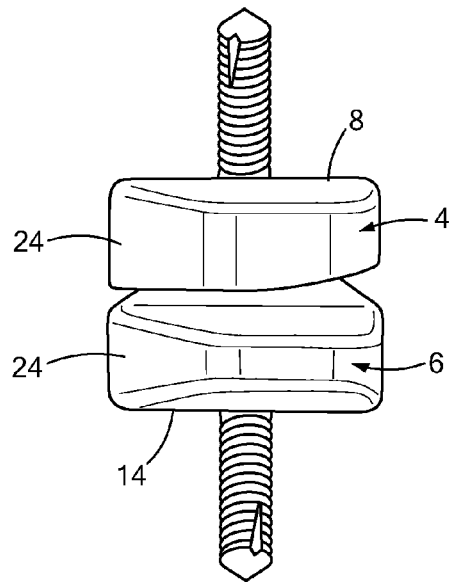 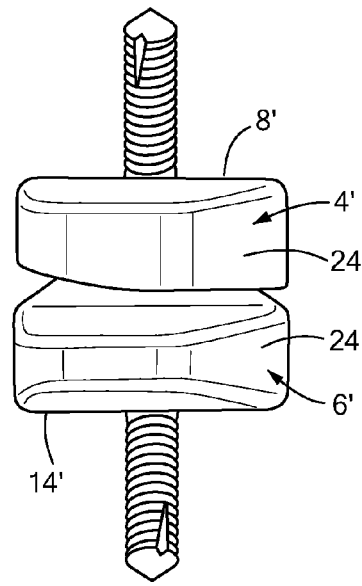
*FIG. 9*  *FIG. 10*
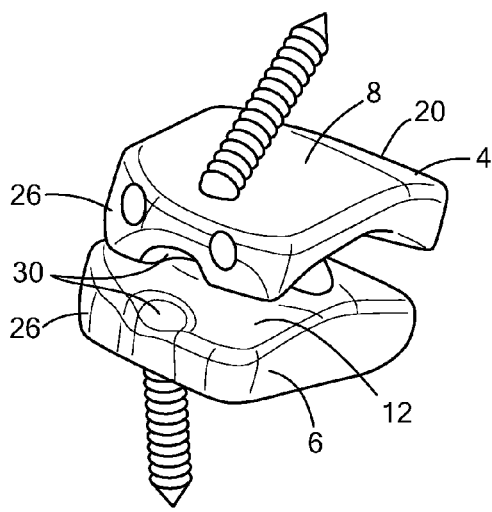 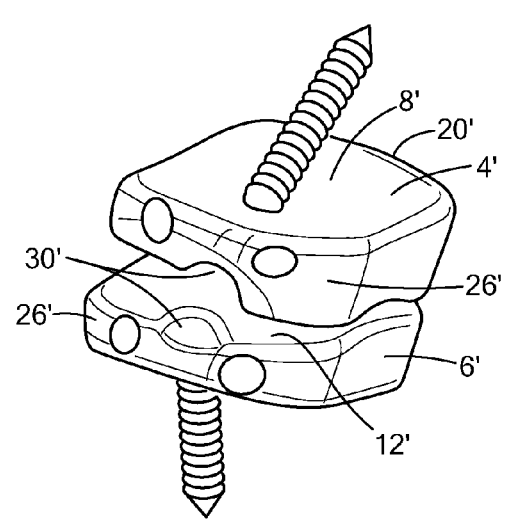
*FIG. 11*  *FIG. 12*

TOP PLATE - TYPE A SOCKET DETAIL

TOP PLATE - TYPE A SOCKET DETAIL

TOP PLATE - TYPE A SOCKET DETAIL

TOP PLATE - TYPE A SOCKET DETAIL
Axial View

TOP PLATE - TYPE A SOCKET DETAIL
M/L View

TOP PLATE - TYPE A SOCKET DETAIL
Solid, inverse representation of socket shape

TOP PLATE - TYPE A SOCKET DETAIL
Anterior angle sweep
Radius sweep
Posterior angle sweep
A/P View

SOCKET OPTIONS

Independent sockets
captive on male sphere
limited sideways
rotation

EXPLODED DETAIL (FIN-TYPE IMPLANTS)

Section A-A

Section A-A

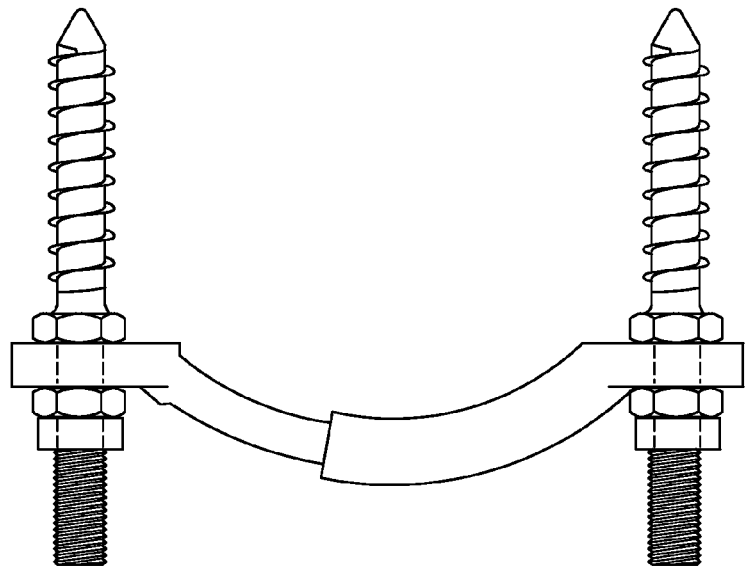
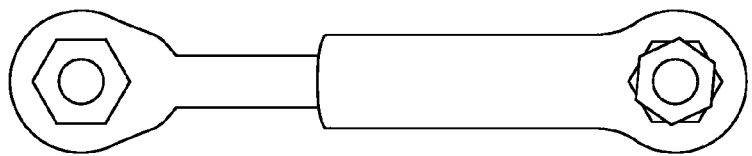
FIG. 44b
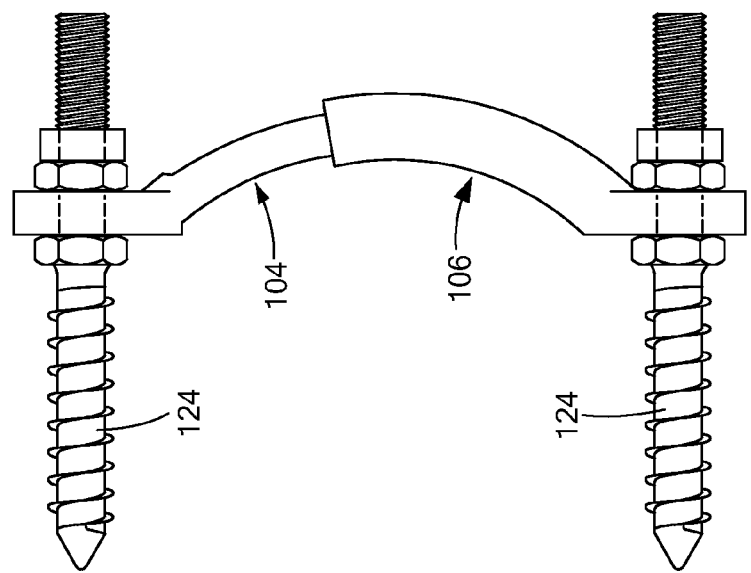
FIG. 44a

FLEXION AND EXTENSION

FLEXION AND EXTENSION

POSTERIORLY INSERTED ARTIFICIAL DISC AND AN ARTIFICIAL FACET JOINT

CROSS-REFERENCE TO RELATED APPLICATIONS

This application is a divisional of pending U.S. patent application Ser. No. 10/970,091, filed Oct. 21, 2004, which claims priority from United Kingdom Patent Application Serial No. 0422963.9, filed Oct. 15, 2004, the entirety of all of which are incorporated herein by reference.

FIELD OF THE INVENTION

This invention relates to devices and surgical methods for the treatment of various types of lumbar spine pathologies. It is specifically directed to the different types of degenerative pathologies in the lumbar spine. It deals with the development of an artificial facet joint, and an artificial lumbar disc replacement that is specifically designed to be inserted from a posterior approach to the spine.

BACKGROUND OF THE INVENTION

Back pain affects 40% of the population. Up to 20% of the population visit their family doctor requesting help with the back problem. Up to 30% of patients continue to complain of significant back pain at one year following the onset of their symptoms.

Although the majority of patients have minor sprains or sins which are self limiting, a significant number of patients go on to develop severe chronic mechanical lower back pain which is caused by inflammatory changes in the lumbar disc associated with degeneration.

Another group of patients with degenerative spine disease go on to develop degenerative spondylolisthesis and spin stenosis. This is a narrowing of the spinal can caused primarily by degenerative changes in the facet join combined with a loss of normal disc eight and buckling of the ligamentum flavum.

Degeneration occurs in a spinal segment. The spin segment consists of the lumbar disc anteriorly and two facet joints posteriorly. This is therefor called a three joint complex. Degenerative changes in the disc can lead to changes in the facet joint and vice versa. In patients with significant lumbar disc degeneration, the facet joints are also usually degenerate.

Pain occurs from all components of the three joint complex, including the facet joints and the disc. The facet joint is in fact a synovial joint and suffers from the problems at are known to affect other synovial joints in the body lie the hip and the ee. The facet joint particularly contributes to degenerate spondylolisthesis and commonly occurs at levels where the facet joints are sagittally orientated, for example at the L4/5 level.

After failing all the conservative treatments available, a minority of patients with back pain or leg pain will go on to require surgical intervention. For patients with predomiantly lower back pain who have a degenerative lumbar disc, some surgeon's consider the solution lies in removing the pain generator which is the disc and restoring normal loading across the disc by doing an inter-body stabilisation procedure.

The two types of inter-body stabilisation procedure currently available an artificial disc replacement performed anteriorly and inter-body fusions performed anteriorly d/or posteriorly. These inter-body stabilisation procedures are often combined with decompression of the spinal canal and the nerve roots if there is nerve root impingement.

As far as ter-body fusions are concerned, there are two basic strategies that surgeons adopt. The first is to perform an anterior inter-body fusion combined with posterior stabilisation externally of the spinal canal. Anterior inter-body fusion on its is still questioned because it does not provide a posterior tension band. An alternative strategy is a posterior lumbar inter-body fusion, where the entire inter-body fusion procedure is performed from behind and it is combined with neural decompression as well as removal of the degenerative facet joints. Posterior lumbar inter-body fusion also provides a posterior tension band. This strategy therefore deals with all three joint components which can generate possible pain at the disc level, including the lumbar disc, the neural structures and the facet joints.

When it comes to lumbar disc arthroplasty procedures, these are performed via an anterior lumbar approach. The disc is removed and an artificial lumbar disc is inserted into the space. This removes the pain generator and allows normal loading across the disc, as well as allowing some movement at this level. The advantage of this is to reduce the strains on the disc above and therefore reduce the chances of adjacent segment degeneration. Several studies have shown that adjacent segment degeneration can occur above a fused segment because of the increased loads being transmitted to is level.

One of the disadvantages of anterior lumbar arthroplasty is that the facet joints at is level continue to move and also continue to act as a pain generator. In addition, if there is any neural impingement, these symptoms can continue. The other disadvantage of anterior lumbar arthroplasty is that the majority of spine surgeons are not familiar with the anterior approach, and although complications are uncommon, they can be life and limb threatening when they do occur.

There is therefore a concern among researchers and the surgical community, that long term results of anterior lumbar disc arthoplasty may be compromised by progressive degeneration of the facet joint at the same level. In addition, after lumbar disc arthroplasty, several patients continue to complain of facet joint pain because of increased loads being placed on the facet joint as a result of the surgical procedure.

At present there is no posterior lumbar arthroplasty procedure available. It is therefore an aim of the present invention to provide an artificial lumbar disc that can be inserted posteriorly, thereby delivering the advantages of approaching the spine posteriorly and removing the disadvantages associated with approaching the spine anteriorly.

It is a further aim of the present invention to provide a facet joint replacement prosthesis.

It is a yet further of the present invention to provide a lumbar prosthetic system that deals with the painful disc, the neural impingement and the pail facet joints by providing a combination of a lumbar disc prosthesis and a facet joint prosthesis as a single unit.

BRIEF SUMMARY OF THE INVENTION

According to a first aspect of the present invention there is provided a lumbar disc prosthesis, sad lumbar disc prosthesis including a pair of disc members, the first member of said disc pair having a vertebral endplate contact surface and a recessed portion on an opposing surface thereof, the second member of said disc pair having a vertebral endplate contact surface and a protruding portion on an opposing surface thereof, the protruding portion of the second member engaging with the recessed portion of the first member in use, and wherein the spinal disc prosthesis includes a further pair of disc members, said further pair of disc members so including first and second members.

Preferably the disc pairs are mirror images of each other.

Thus, the present invention provides a lumbar disc prosthesis having two disc member pairs and thus two separate articulating portions, one articulating portion on each pair of disc members. The disc member pairs are each independently inserted into the disc space on either side of the dural sac in use through the trans-foraminal or posterior route bilaterally and are provided a spaced distance apart in use to allow accommodation in accordance with the anatomy of the lateral aspect of the disc space. Thus, the disc prosthesis can be inserted through the posterior route whilst taking into account the neural anatomy posteriorly.

The lumbar disc prosthesis of the present invention can be inserted at all levels between L2 and the sacrum, typically depending on the level of expertise of the operating surgeon.

Preferably the first members of each disc pair are provided in the left and right areas of the disc space respectively in use. The second members of each disc pair are also provided in the left and right areas of the disc space respectively in use. Thus, each pair of members constitutes a left and right lumbar disc prosthesis.

Preferably the recessed portion of the first member is substantially curved and the curvature of the medial part of said recessed portion is asymmetrical to the curvature of the lateral part of said recessed portion.

The purpose of this asymmetry the medial-lateral plane is to allow "capture" of the protuding portion of the second member. such at when two pairs of disc prostheses are placed in the patient, the two vertebrae can move from side to side as well as anteriorly and posteriorly.

Preferably the lateral part of the recess has curvature corresponding to an arc of a circle which has a radius greater that of an arc of a circle corresponding to the curvature of the medial part of the recessed portion. Further preferably the radius of the lateral part is at least twice as big as the radius of the medial part.

Preferably an anterior part of the recessed portion is substantially symmetrical to a posterior part of the recessed portion.

The protrusion portion of the second member is typically of different shape and/or dimensions to the recessed portion of the first member. Thus, the protrusion portion is asymmetrical or forms an asymmetric fit with the recessed portion.

Preferably the protrusion portion is substantially dome shaped and makes contact with only a part of the recessed portion when assembled. Preferably the recessed portion is substantially an inversed dome shape.

The protrusion portion is symmetrically symmetrical the anterior-posterior plane and in the medial to lateral plane. The curvature, the medial to lateral plane can be the same or different to that in the anterior to posterior plane.

Preferably the inner or opposing surfaces of each of the first and second disc members are provided with at least three sections; a middle section and at least two end sections, the recessed and protruding portions being provided in the middle section of the respective disc members.

Preferably the thickness or depth of the first disc member is less adjacent the middle section or recessed portion compared to the two end sections thereof.

The middle and end sections of each disc member are typically arranged transversally along the length thereof, i.e. the boundaries of adjacent sections are provided between the medial to lateral sides of the disc members.

Preferably one or bot ends of the first and second disc members have a narrowing taper (i.e., the prosthesis as a whole has a narrowing taper). This narrowing taper is as a result of the outer or vertebral end plate contact surface of said first and/or second disc member being provided at an acute angle with respect to the horizontal at one or both ends. These angled surfaces are preferably substantially planar in form. For example, the outer or vertebral end plate contact surface of the first disc member slopes downwardly towards the ends of the disc member and/or the outer or vertebral end plate contact surface of the second disc member slopes upwardly towards the ends of the disc member. The narrowing taper of the prosthesis allows easy insertion of the prosthesis in the disc space via a posterior route.

In one embodiment, the narrowing taper is provided at an anterior end of the prosthesis. Thus the outer surfaces or vertebral endplate contact surfaces of the disc member(s) slope towards the opposing surfaces thereof at the anterior end of the disc member(s). This provides a "lead in" feature which increases the ease with which the front of the prosthesis can be inserted via a posterior route into the disc space.

In one embodiment, a narrowing, taper is provided at the posterior end of the prosthesis. Thus, the outer surfaces or vertebral endplate contact surfaces of the disc member(s) slope towards the opposing surfaces thereof at the posterior end of the disc member(s). The posterior angled face allows the prosthesis in the neutral position to be placed such that the vertebral end plates are in lordosis The posterior end of the prosthesis typically slopes or tapers in an opposite direction to the anterior end.

Preferably the anterior end slope is substantially smaller than the posterior end slope.

Preferably one or both end sections of the inner or opposing surfaces of said first and/or second members are provided at an acute angle to the horizontal. For example, the inner end section surface of said first member can slope downwardly towards one or bot ends of said member. The inner end section surface of said second member can slope downwardly towards the one or both ends of said member.

Further preferably the outer and inner surfaces of said second disc member for a narrowing taper towards one or both ends of said disc member.

Further preferably the outer and inner surface of said first disc member form a narrowing taper adjacent an end of said disc member in which attachment screws are to be located therethrough.

The geometry of the middle and end sections of the first and second disc members allow contact to be made between the recessed and protrusion portions thereof and for a gap to be formed adjacent the end sections of the disc members when the prosthesis is in a neutral position. When the prosthesis is in extension or flexion (i.e. the upper or first disc member moves towards the posterior or anterior end of the lower or second disc member), the gap between the end sections at the opposite end increases, thereby causing the annulus in which the disc prosthesis is located to tighten. Due to the geometry of the planar slopes within the prosthesis the annulus will tighten not only posteriorly in flexion but laterally as well.

Preferably the vertebral endplate contact surface of the first and/or second members of each disc pair is provided with attachment means for allowing attachment of the disc member to an adjacent disc in use.

The attachment means include one or more apertures for the location of screws and/or any other suitable attachment device therewith, one or more tapered members or fins and/or any other conventional attachment apparatus.

The first and second members of each pair typically correspond to upper and lower disc members. The superior surface of the lower disc member has a protrusion thereon and the inferior surface of the upper disc member has a captive recess or socket thereon.

Preferably the recessed portion has two sloped surfaces associated therewith, typically corresponding to the end sections thereof, one surface leading anteriorly to the edge of the inferior surface and one surface leading posteriorly to the edge of the inferior surface. These sloping surfaces can be planar or can be slightly concave in form.

The lumbar disc prosthesis can be used in conjunction with a facet joint prosthesis also provided posteriorly to provide a system which can work together as a single unit to replace the painful discs overcomes neural impingement and painful facet joints.

Preferably the facet joint prosthesis typically includes a first member for attachment to a first vertebra of a corresponding disc and a second member for attachment to a second vertebra of a corresponding disc in use, and wherein at least a part of said first member is telescopically mounted in at least a part of said second member in use.

Preferably the first and second members are elongate members and the provision of one telescopically mounted in the other allows the distance between pas of the first and second members to be increased and/or decreased as required.

The first vertebra is typically an upper vertebra and the second vertebra is typically a lower vertebra.

The facet joint prosthesis allows replacement of existing facet joints to be undertaken at all lumbar levels from T12 to the sacrum.

The interconnecting first and second members are formed such that they can articulate to allow flexion-extension, small degrees of rotation and side to side flexion.

Preferably securing means are provided for insertion of the first and second members into each of the vertebral bodies above and below the disc between which the facet joint prosthesis is to be located. The first and second members can then be secured to said securing means. A plurality of first and second members can be attached to the securing means if required to form a stack, thereby allowing facet joint replacement at multiple levels within the spine.

The securing means include any suitable type of surgical securing device, such as a pedicle screw.

According to a second aspect of the present invention there is provided a lumbar disc prosthesis, said lumbar disc prosthesis including a pair of disc members, the first member of said disc pair having a vertebral endplate contact surface and a recessed portion on an opposing surface thereof, the second member of said disc pair having a vertebral endplate contact surface and a protruding portion on an opposing surface thereof, the protruding portion of the second member engaging with the recessed portion of the first member in use, and wherein the recessed portion of the first member is substantially curved and the curvature of the medial par of said recessed portion is asymmetrical to the curvature of the lateral part of said recessed portion.

According to a third aspect of the present invention there is provided a facet joint prosthesis, said prosthesis including a first member for attachment to a first lumbar disc in use and a second member for attachment to a second lumbar disc in use, and wherein at least a part of said first member is telescopically mounted in at least a part of said second member in use.

The facet joint prosthesis can be used alone or in combination with the lumbar disc prosthesis of the present invention or with any other lumbar disc prosthesis. The facet joint replacement procedure of the present invention alone will have a role in the treatment of patients with spinal stenosis and adjacent level disc disease, where some stability is required at the disc level without fusing a particular disc segment. The facet prosthesis can partially constraining certain degrees of motion.

According to further independent aspects of the present invention ere is provided a prosthesis system including a lumbar disc prosthesis and a facet joint prosthesis as hereinbefore described; a first or upper disc member for inclusion in a lumbar disc prosthesis pair; a second or lower disc member for inclusion in a lumbar disc prosthesis; a method of insertion of a lumbar disc prosthesis in a patient via a posterior route and a method of insertion of a facet joint replacement prosthesis in a patient via a posterior route.

Thus, the present invention overcomes the problems and disadvantages associated with current disc replacement strategies. It has the benefits associated with posterior lumbar inter-body fusion surgery, but at the same time it allows movement at that level and reduces the strain on adjacent discs and tee risks of adjacent segment disc failure. This invention also address all three pain generators at the lumbar disc level including the degenerative disc, the impingement of the neural structures, and the facet joint.

BRIEF DESCRIPTION OF THE DRAWINGS

FIGS. 1-30 relate to a lumbar disc prosthesis according to embodiments of the present invention aid FIGS. 31-50 relate to a facet joint replacement prosthesis according to embodiments of the present invention.

FIG. 1 is a side view of a lumbar disc prosthesis according to one embodiment of the present invention;

FIGS. 2-4 show the prosthesis in FIG. 1 with the upper disc member in extension, flexion and in a neutral position respectively;

FIGS. 5 and 6 show the superior surfaces of the upper members of the left and right lumbar prosthesis pairs respectively;

FIGS. 7 and 8 show rear views of the left and right lumbar prosthesis pairs respectively;

FIGS. 9 and 10 show front views of the left and right lumbar prosthesis pairs respectively;

FIGS. 11 and 12 show oblique views of the left and right lumbar prosthesis pairs respectively;

FIGS. 13 and 14 show the superior surfaces of the lower members of the left and right lumbar prosthesis pairs respectively;

FIGS. 15 and 16 show rear views of the lower members of the left and right lumbar prosthesis pairs respectively;

FIG. 17 is a side view of the lower member of a lumbar prosthesis;

FIGS. 18 and 19 show front views of the lower members of the left and right lumbar prosthesis pairs respectively;

FIGS. 20 and 21 show oblique views of the lower members of the left and right lumbar prosthesis pairs respectively;

FIG. 22 is a side view of an upper member of a lumbar prosthesis pair to illustrate the angulations and geometry of the inferior surface thereof;

FIG. 23 is a front view of the upper member of the lumbar prosthesis pair to illustrate the radius in the medial and lateral part of the curvature of the inferior surface;

FIG. 24 is an oblique view of the upper member of the lumbar prosthesis pair to further illustrate the shape of the inferior articulating surface thereof;

FIG. 25 shows a perspective view of the inferior surface of the upper members of the left and right lumbar prosthesis pairs respectively;

FIG. 27 is a cross section through the upper member of a lumbar prosthesis pair showing the medial lateral curvature of the articulating surface;

FIG. 28 show front views of the left and right lumbar prosthesis pairs respectively in an alternative embodiment with the screws replaced by fin members;

FIGS. 44a-44d illustrate a side view, front view, perspective view from the rear and perspective view fin the front of the facet joint replacement prosthesis in FIG. 31;

DETAILED DESCRIPTION OF THE PREFERRED EMBODIMENTS

Lumbar Disc Prosthesis

Figure 1:
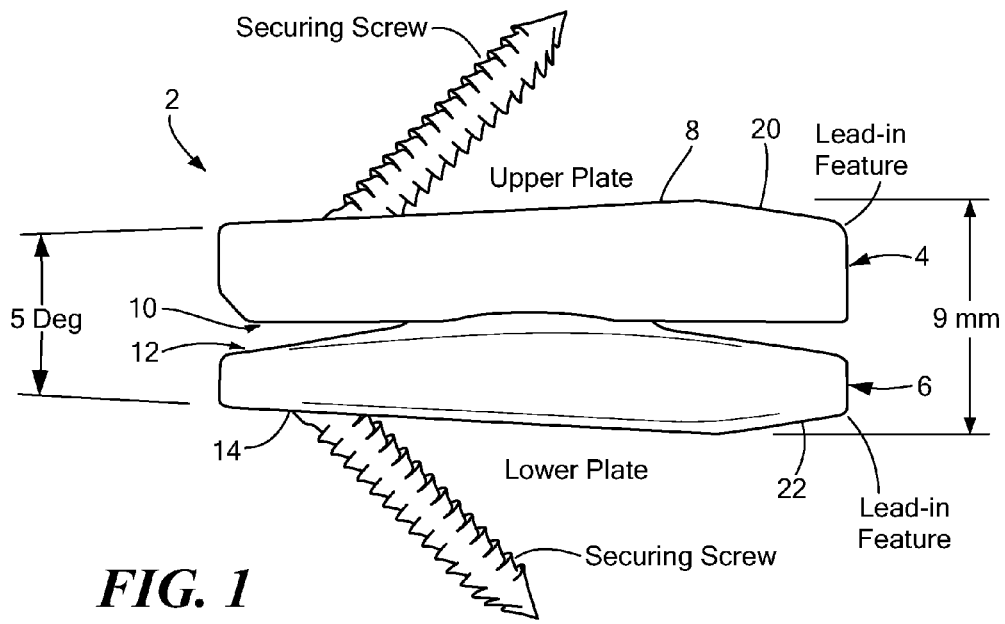

Referring firstly to FIGS. 1-30, there is illustrated a lumbar disc prosthesis 2 which can be inserted into a lumbar disc space via a posterior route as a replacement for a diseased and/or damaged lumbar disc.

The disc prosthesis 2 includes two pairs of disc members, each pair including an upper disc member 4, 4' and a lower disc member 6, 6'. (Use of a reference numeral with thereafter refers to a second or further feature equivalent to the feature indicated by the reference numeral alone. Thus, disc member 4 refers to the first prosthesis pair upper member and disc member 4' refers to the second prosthesis pair upper member). The upper and lower disc members 4, 6; 4', 6' of each pair constitute a left and right disc prosthesis respectively. These disc members are shaped and dimensioned such that they can be inserted into a lumbar disc space either side of the dural sac whilst taking into account the posterior neural anatomy Each upper disc member 4, 4' includes a vertebral endplate contacting surface or superior surface 8, 8' ad an inferior surface 10, 10'. Each lower disc member 6, 6' includes a superior surface 12, 12' and a vertebral endplate contacting surface or inferior surface 14, 14'.

A dome shaped protrusion 16 is formed substantially centrally of superior surface 12 of lower disc member 6. Protrusion 16 is received in a substantially central recess 18 on inferior surface 10 of upper disc member 4 as will be described in more detail below.

Both the superior surface 20 of upper member 4 and the inferior surface 22 of lower member 6 are, angled to provide the prosthesis with a "lead in" or narrowing tapered feature. This lead in feature allows the prosthesis to enter the posterior disc space which is narrower than the anterior disc space. In addition to the lead feature which is provided at the anterior or font end 24 of the prosthesis members, each prosthesis pair has a lordosis or narrowing taper angle towards the posterior or rear end 26 of the prosthesis members between the inferior surface 14 of the lower disc member 6 and superior surface 8 of the upper member 4 of approximately 6 degrees (this angle or any other angle mentioned hereinafter is for exemplary purposes and does not limit the invention in any way), as shown in FIG. 1. This makes the outer surfaces of the disc prosthesis pairs at the posterior and anterior ends substantially wedge shaped or tapered to allow ease of insertion into the disc space. The taper or angle of the outer surfaces at the posterior end is in an opposite direction to the taper or angle of the outer surface at the anterior end.

With reference to FIGS. 1-27, the superior surface of upper disc member 4 and the inferior surface of lower disc member 6 have attachment means in the form of screws 28 to allow attachment of the disc prosthesis to adjacent vertebrae when positioned in a patient. Apertures 30 are provided on the inferior and superior surfaces 10, 12 of the upper and lower disc members 4, 6 respectively of the prosthesis pairs to allow the insertion of screws 28 through the prosthesis disc members. The screws typically fitted from the posterior end 26 and the screws and interior wails defining apertures 30 are provided at an acute angle to the vertical to allow ease of attachment. Apertures 30 and screws 28 within each pair diverge outwardly away from each other towards anterior end 24. The inferior surface on which these apertures are provided on the upper disc member is angled such that it slopes upwardly towards the superior surface of the upper disc member. The superior surface on which these apertures are provided on the lower disc member is angled such that it slopes downwardly towards the inferior surface of the lower disc member, thereby forming a narrowing taper at the posterior end of the lower disc member. These angled surfaces typically form, at least part, the posterior end segments of the inferior and superior surfaces 48, 38 of the upper and lower disc members 4, 6 respectively. This feature is to allow ease of insertion of screws or other attachment means to anchor the prosthesis into the vertebra.

Figure 2:
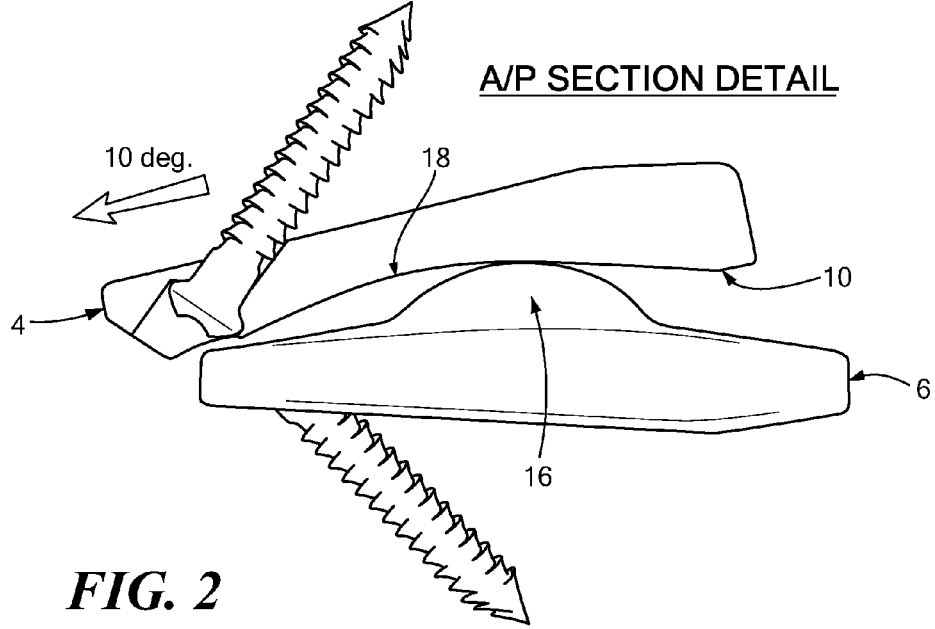

With the protrusion 16 on lower member 6 located in recess 18 of upper member 4 when the prosthesis is assembled, relative movement between the upper and lower members 4, 6 allows the prosthesis to undergo extension and flexion. The substantially dome shaped protrusion 16 contacts only a par of the recess 18 due to differences in symmetry and geometry. In the example illustrated, the upper member 4 can move with respect to the lower member 6 through approximately to degrees in a posterior direction to allow extension of the prosthesis, as shown in FIG. 2. Due to the nature of the inferior surface 10 of upper disc member 4, as the upper member 4 goes into extension there is an increased distance adjacent anterior end 24 between the upper and lower members 4, 6. This results in a tightening of the annulus anteriorly, as is seen in physiological extension in the disc.

Figure 3:
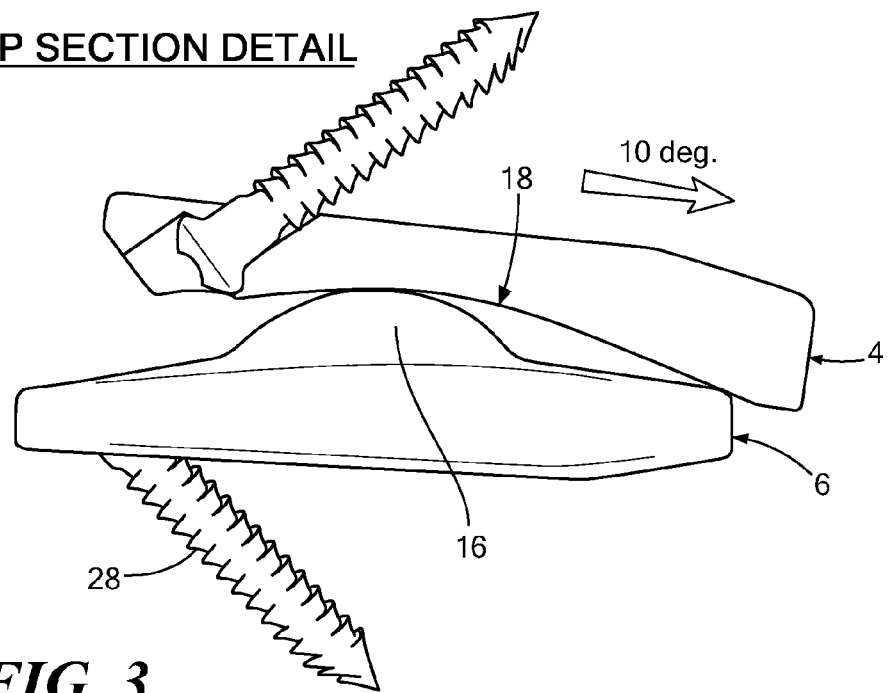
Figure 4:
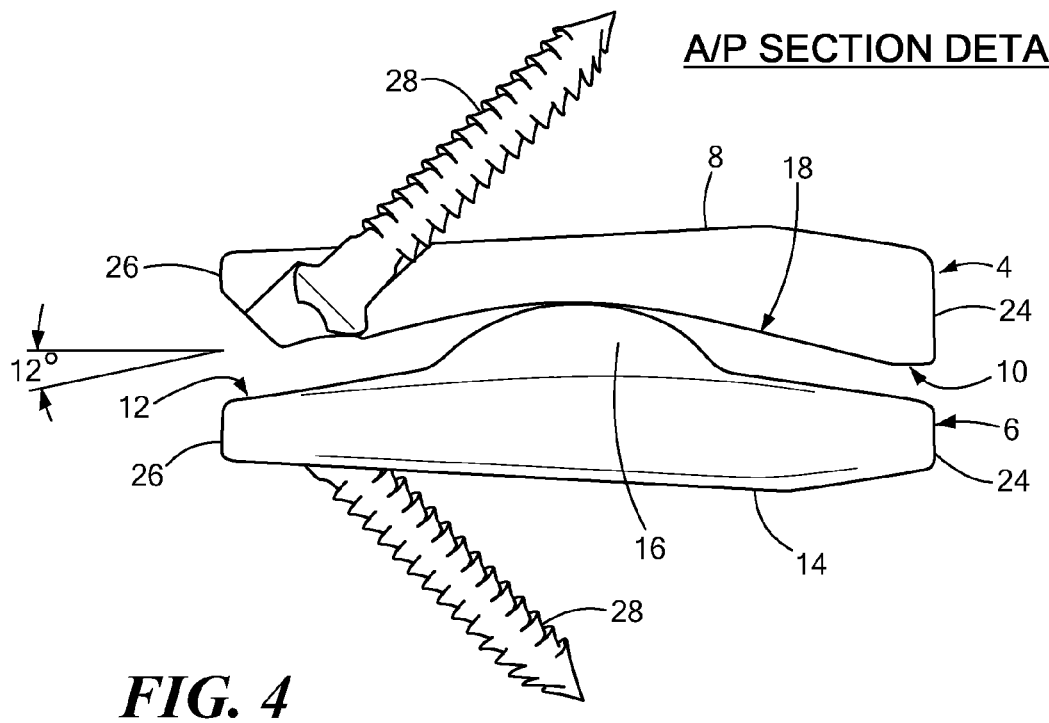
Figure 5:
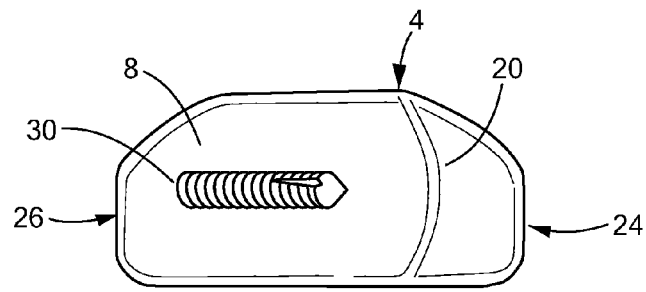
Figure 6:
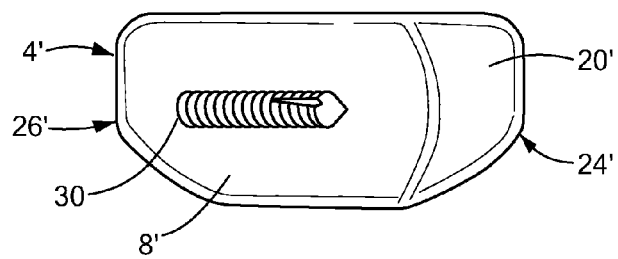
Figure 7:
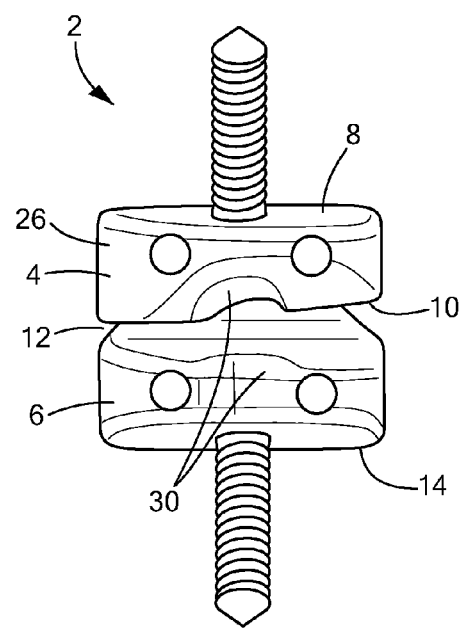
Figure 8:
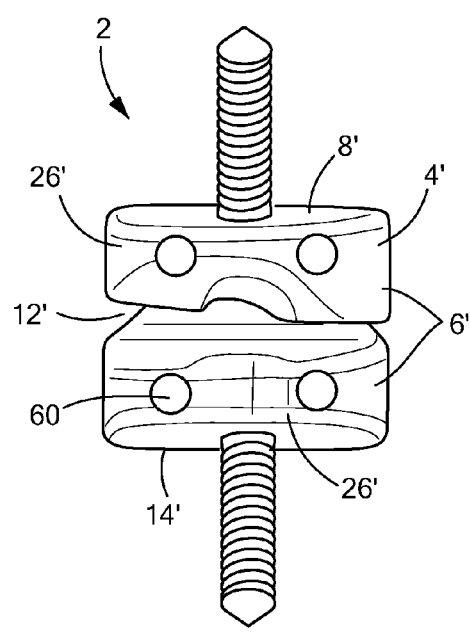
Figure 13:
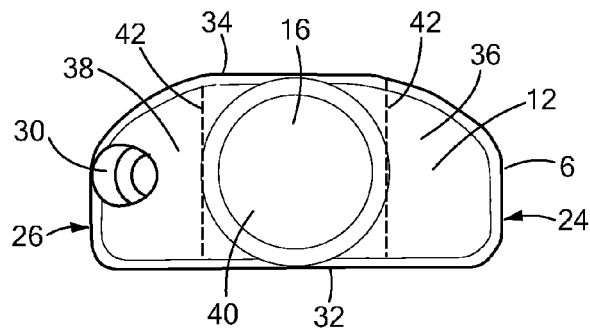
Figure 14:
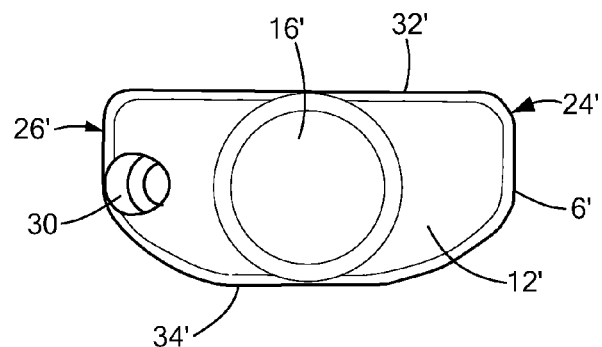
Figure 15:
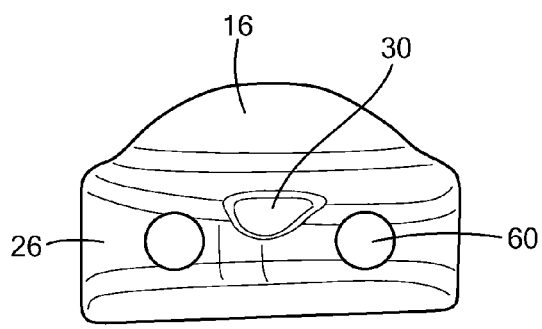
Figure 16:
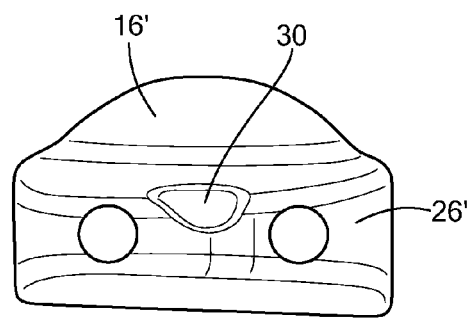
Figure 17:
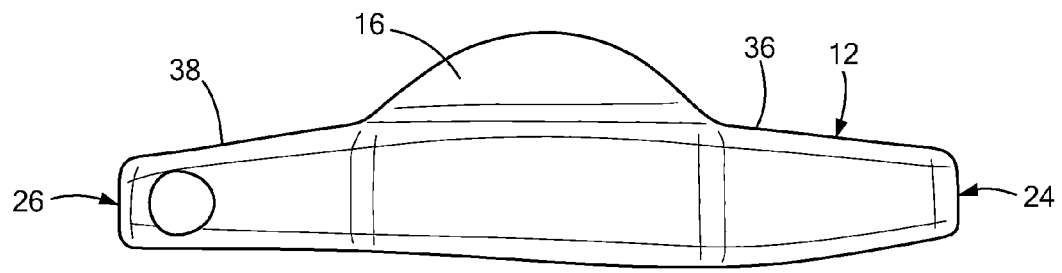
Figure 18:
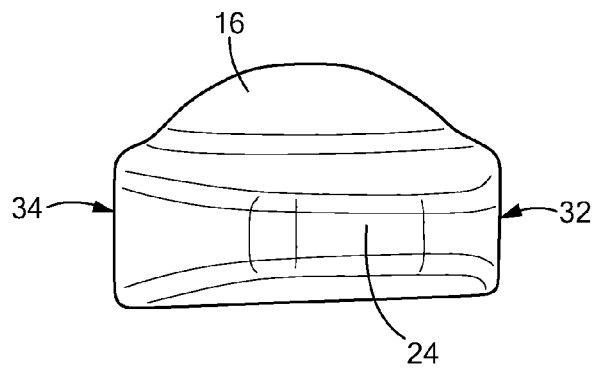
Figure 19:
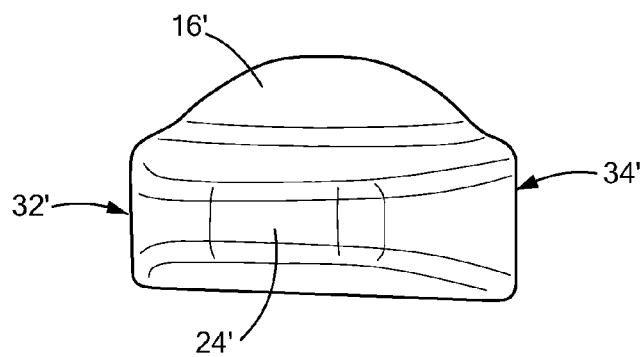
Figure 20:
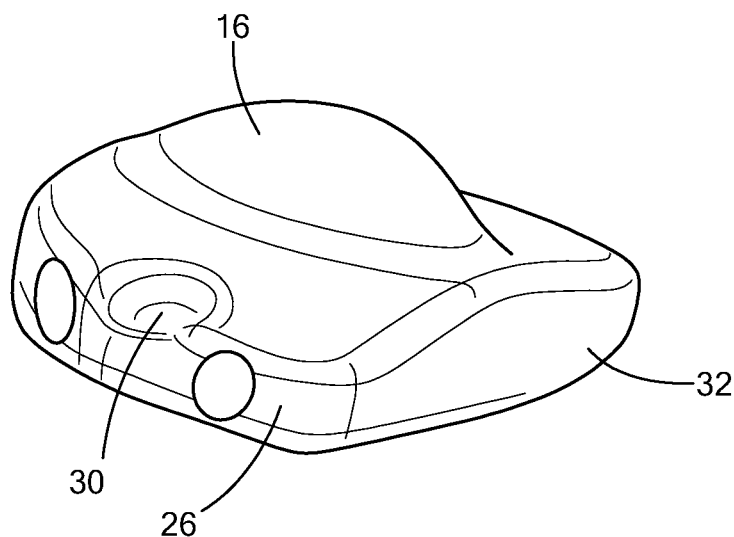
Figure 21:
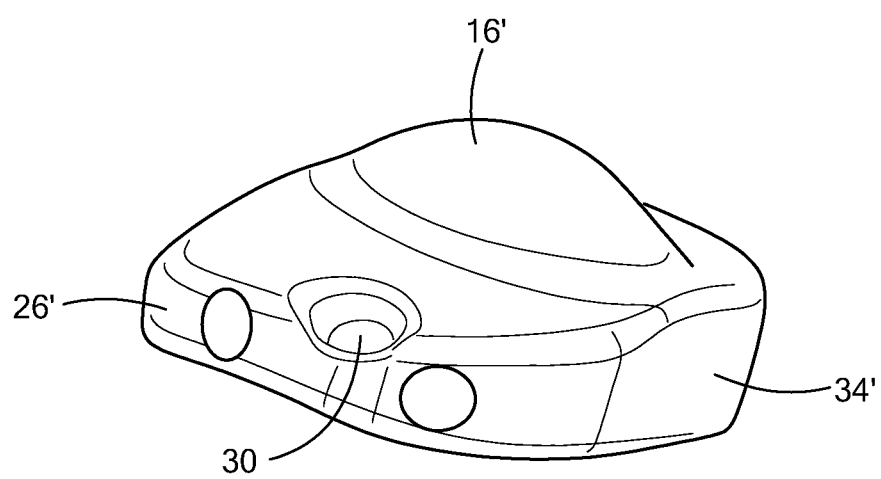

The upper member 4 can also move with respect to lower member 6 through approximately 10 degrees in an anterior direction to allow flexion of the prosthesis, as shown FIG. 3. Again, due to the nature of inferior surface 10, as upper member goes into flexion there is in increased distance adjacent posterior end 26 between the upper and lower members 4, 6. This results in a tightening of the annulus posteriorly and serves as a natural block to further flexion.

Referring to FIGS. 13-21, there are shown more detailed views of lower disc prosthesis member 6, 6'. The dome shaped protrusion 16 is located in a central or intermediate section of superior surface 12 in the anterior to posterior plane. The anterior and posterior end sections 36, 38 either side of the dome section 40, as shown by dotted lines 42, are provided at an acute angle to the horizontal sloping downwardly from intermediate section 40 towards ends 24, 26 respectively. The angled surfaces 36, 38 are typically substantially planar in form. This downwards inline is to accommodate the flexion and extension of the upper disc member 4 without impingement therewith. In the medial and lateral plane, protrusion 16 extends substantially the entire distance between the sides of the prosthesis member or from the medial to the lateral edges 32, 34 respectively.

Referring to FIGS. 22-27, there is illustrated more detailed views of upper disc member 4 showing in particular the curvature and complex geometry of the inferior surface 10. The surface 10 is divided into three distinct regions as with the superior surface of lower disc member 6; a substantially central or intermediate section 44 and anterior and posterior end sections 46, 48 respectively. Each section typically occupies approximately one third of the inferior surface.

The central section 44 is substantially curved and forms an asymmetrical inverse dome shaped recess 18. The curvature of the recess in the medial half (i.e. portion adjacent medial edge 32) of the central section differs to the curvature of the recess in the lateral half (i.e. portion adjacent the lateral edge 34) of the central section. More specifically, the medial half of the dome has a curvature corresponding to the arc of a circle having a radius of approximately 15 mm as shown by arrow 50 whereas the lateral half of the dome has a curvature corresponding to the arc of a circle having a radius of approximately 40 mm, as shown by arrow 52 in FIG. 23. Thus, the curvature of the lateral half of the central section corresponds to an arc of a circle having a radius at least double that of the arc of a circle corresponding to the curvature of the medial half of the central section. The purpose of is asymmetry in the medial/lateral plane is to allow capture of the "dome" shaped protrusion 16 of the lower disc member, but still allow some medial and lateral movement of the disc members. This contributes to stability and prevents dislocation of the upper and lower disc members during movement. The shorter curvature of the medial half of the central section relative to the lateral half helps in the medial and lateral movement of the two vertebral bodies on the right and left prosthesis.

Figure 22:
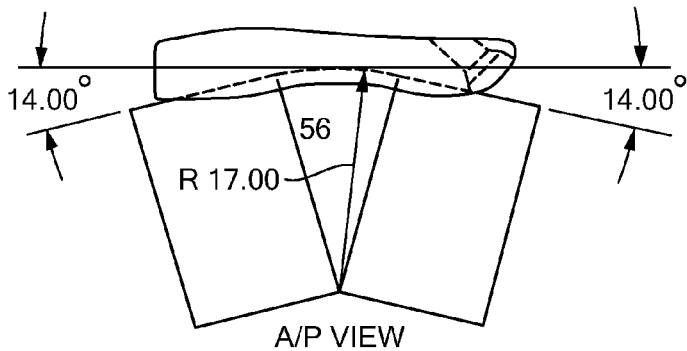
Figure 23:
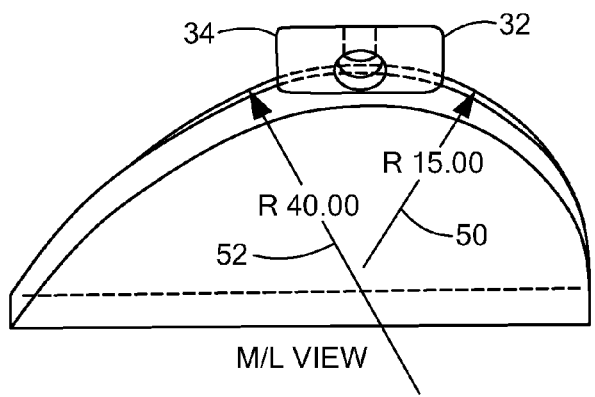
Figure 24:
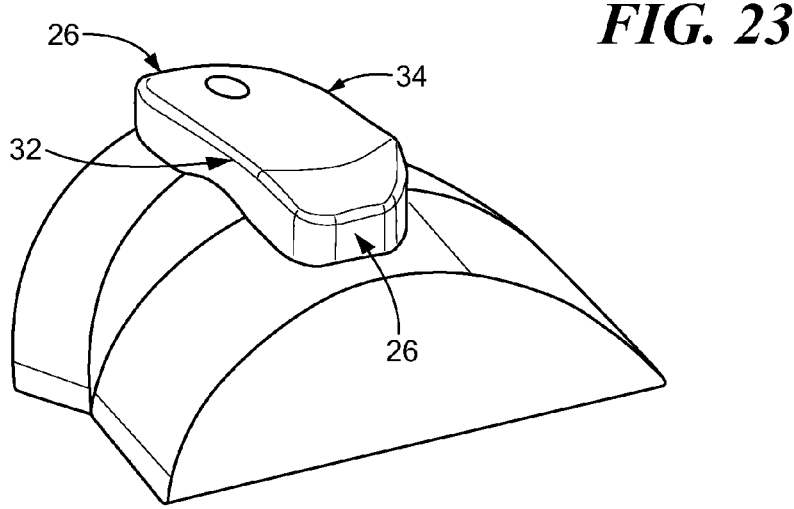
Figure 25:
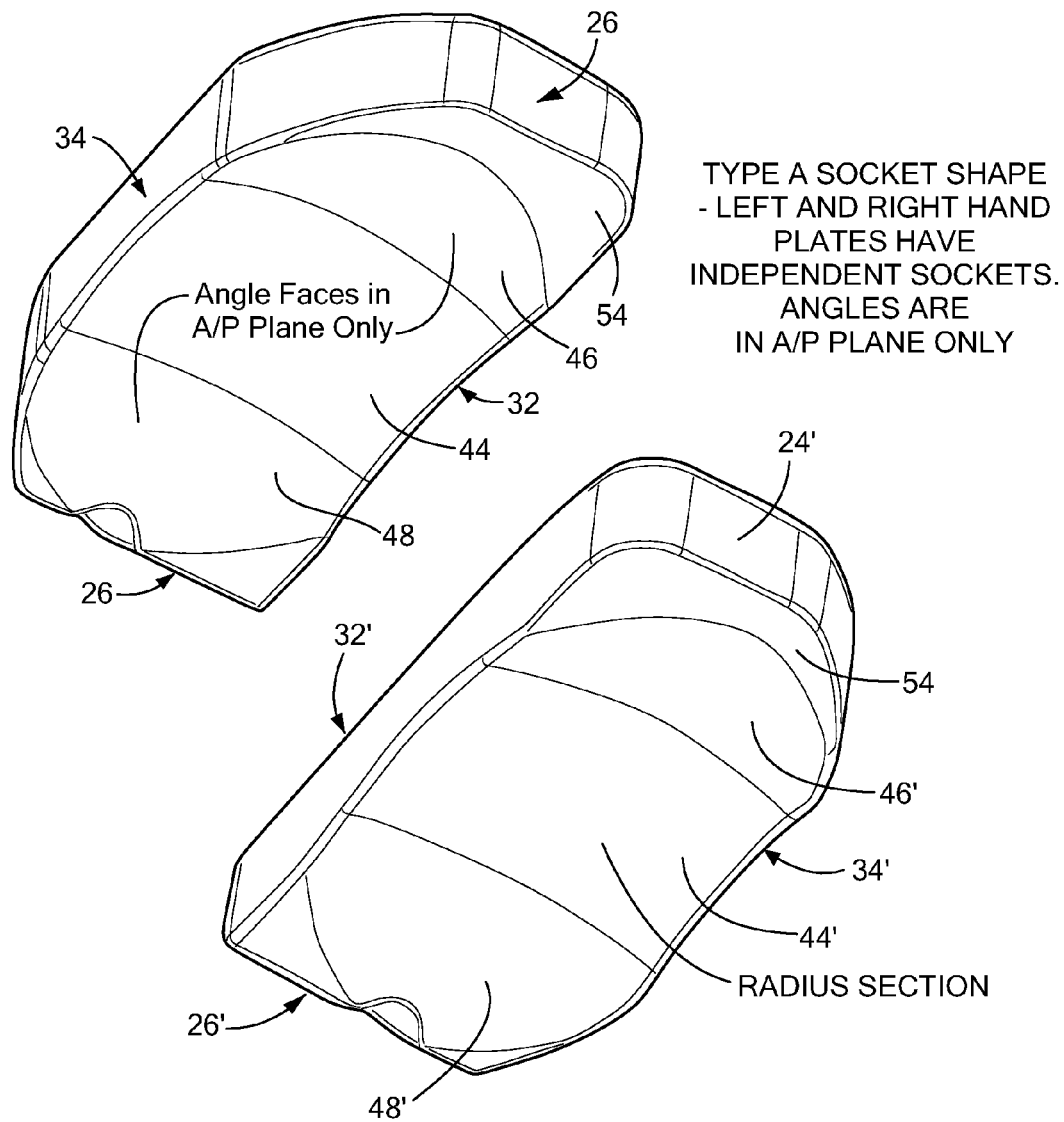
Figure 26B:
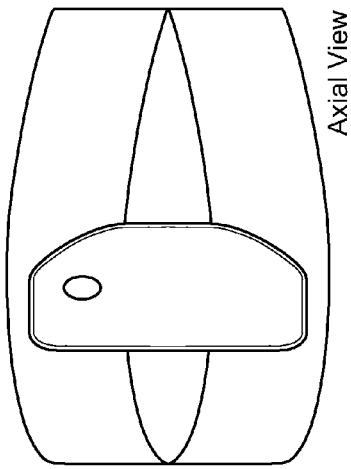
FIGS. 26a-d illustrates a) a solid inverse representation of the recess portion shape on the inferior surface of the upper member of the prosthesis b) an axial view of the prosthesis c) a side view and d) a front view showing the media/lateral asymmetry of the prosthesis.
Figure 26D:
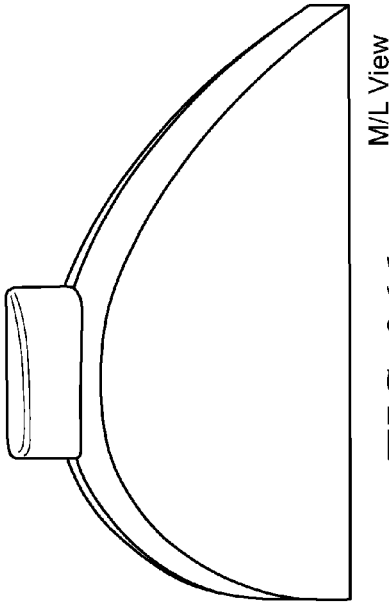
Figure 26A:
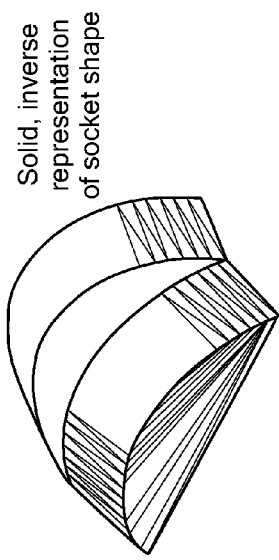
Figure 26C:
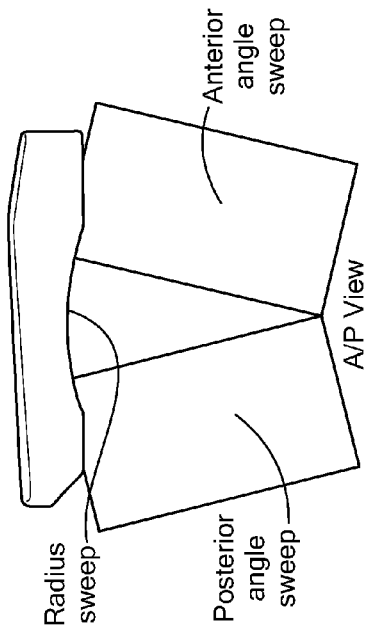
Figure 27:
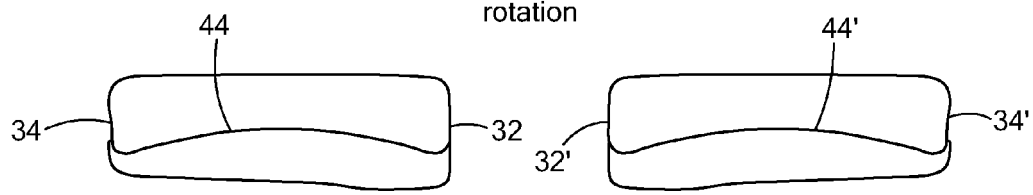
Figure 28:
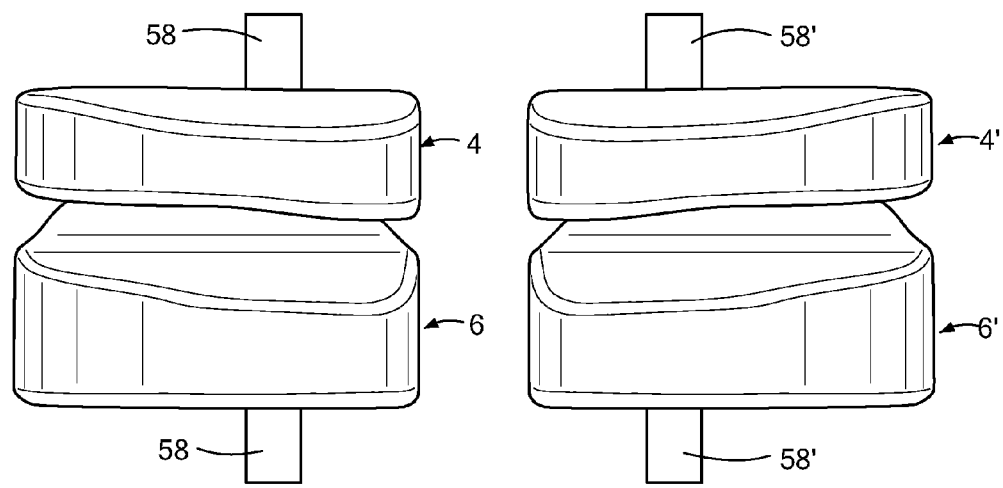
Figure 29A:
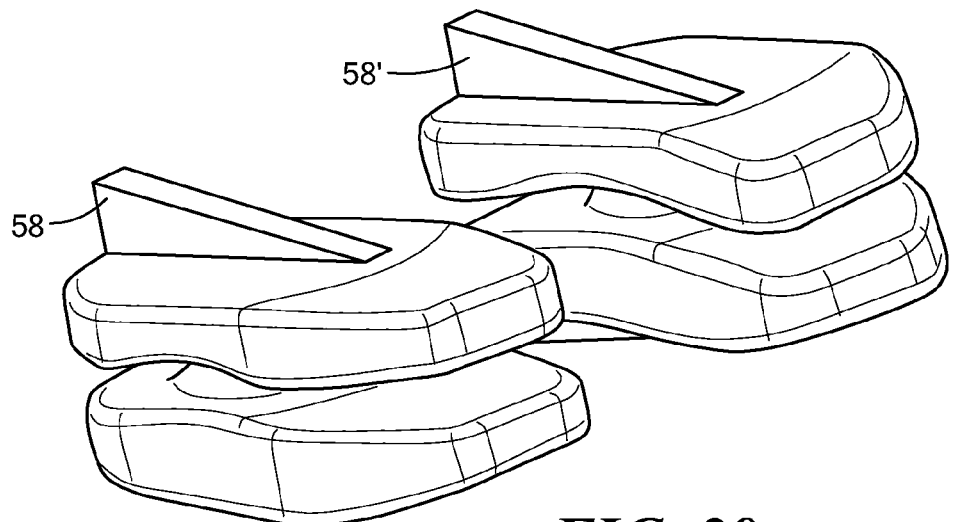
FIGS. 29a and 29b illustrate oblique views of the left and right lumbar prosthesis pairs FIG. 28 joined together and spaced apart respectively.
Figure 29B:
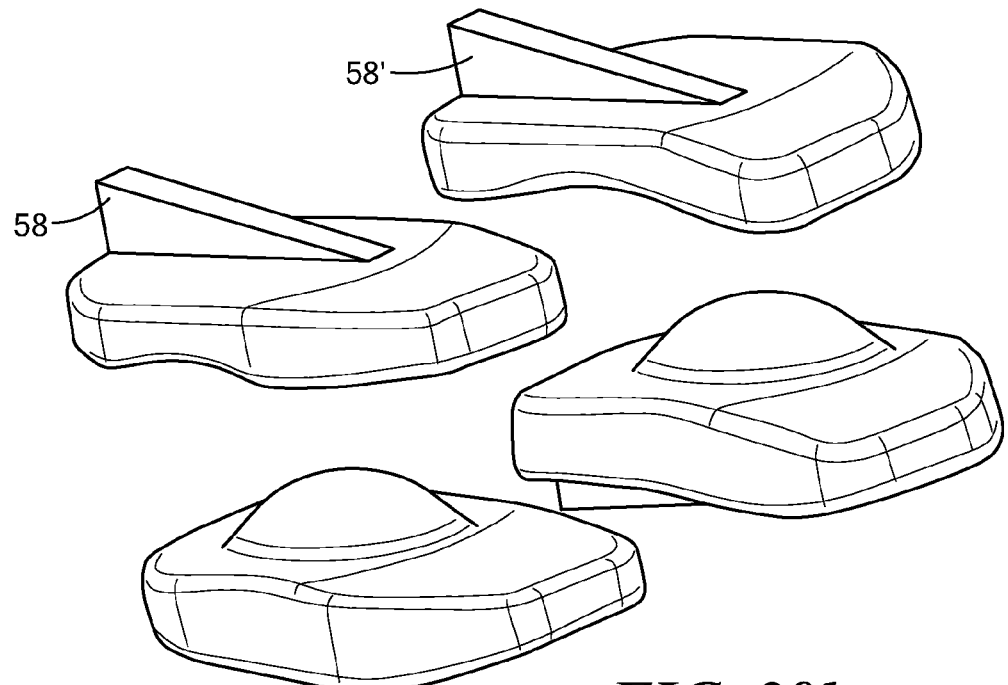
Figure 30A:
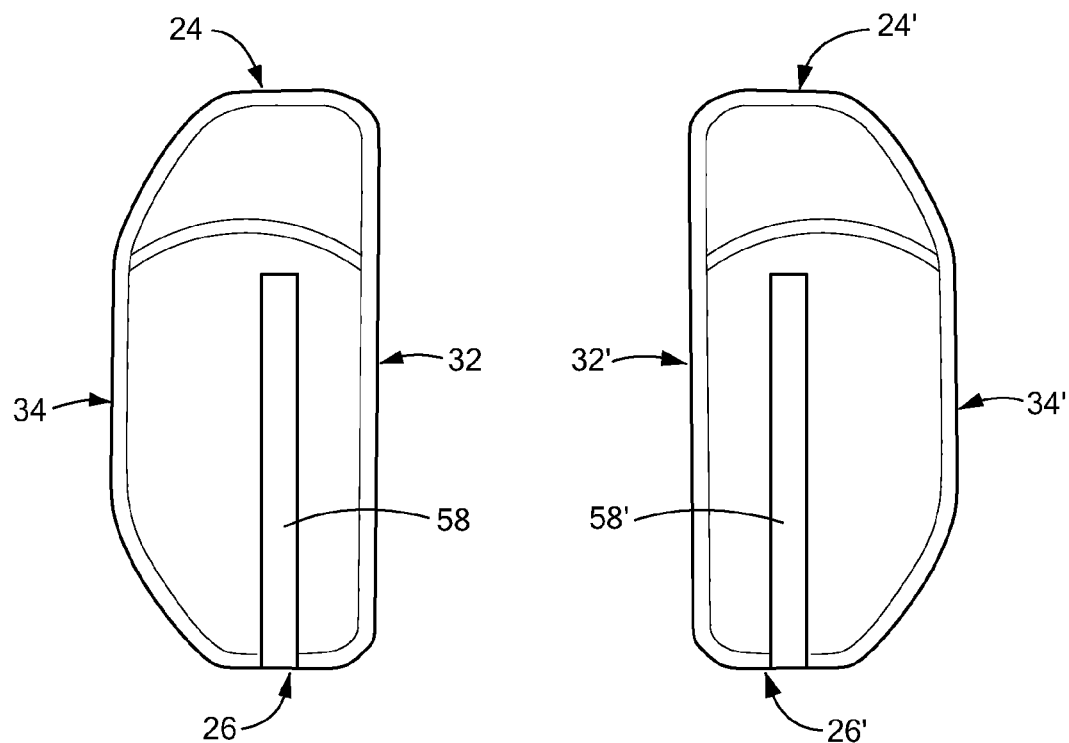
FIGS. 30a-30f show a) superior surfaces of the upper members of the left and right lumbar prosthesis pairs in FIG. 28 b) a side view c) a front view d) a further side view e) inferior surfaces of the lower members of the left and right lumbar prosthesis pairs and f) oblique views of the pairs.
Figure 30B:
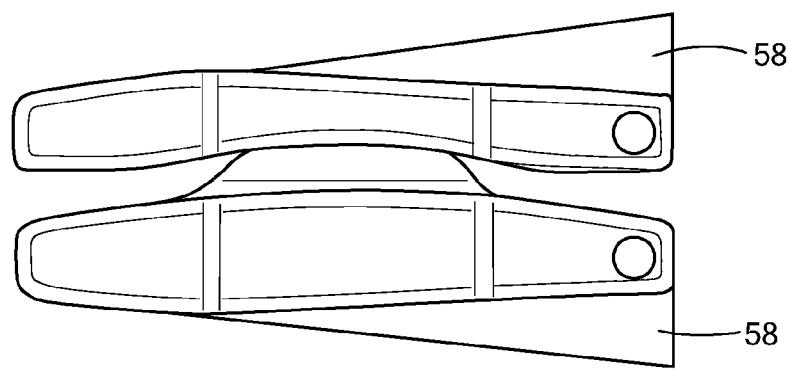
Figure 30C:
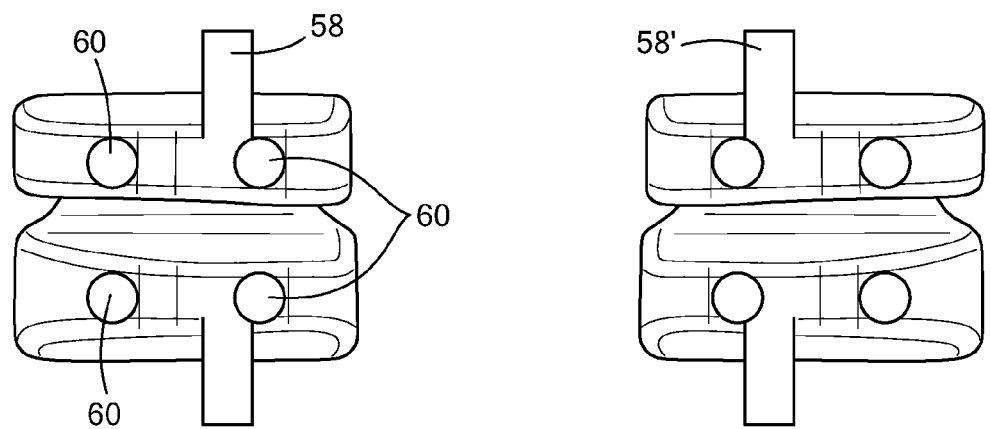
Figure 30D:
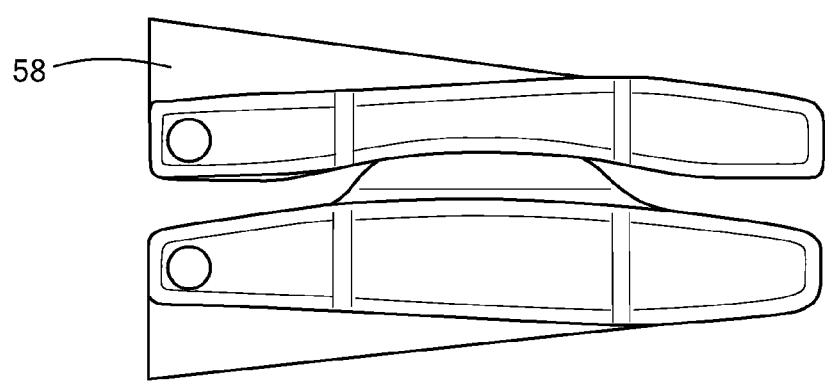
Figure 30E:
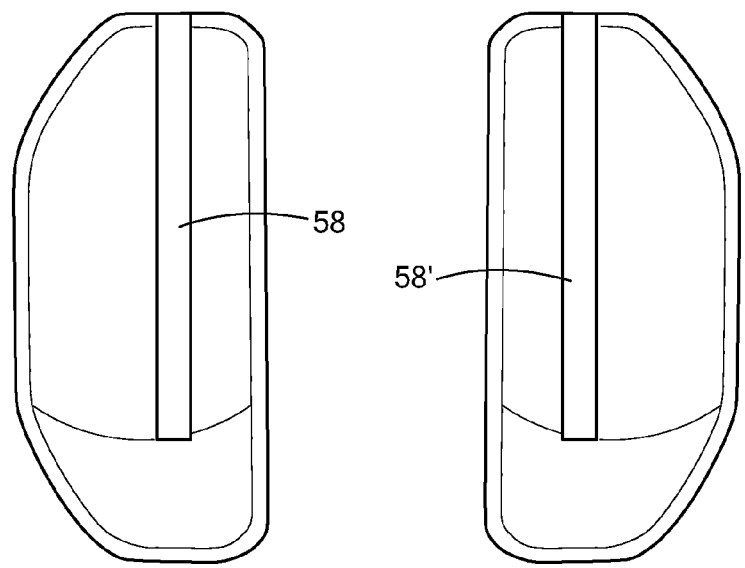
Figure 30F:
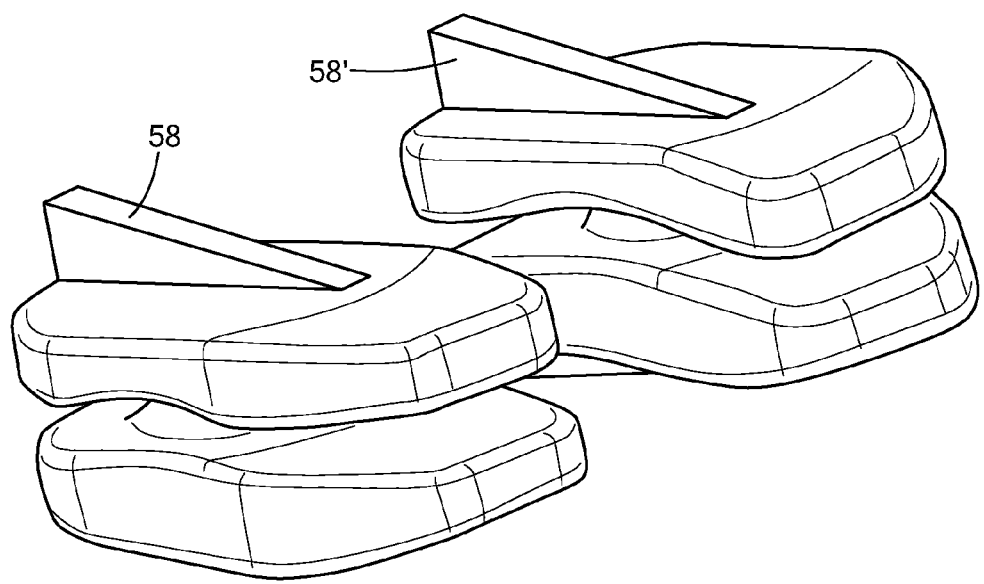
Figure 31:
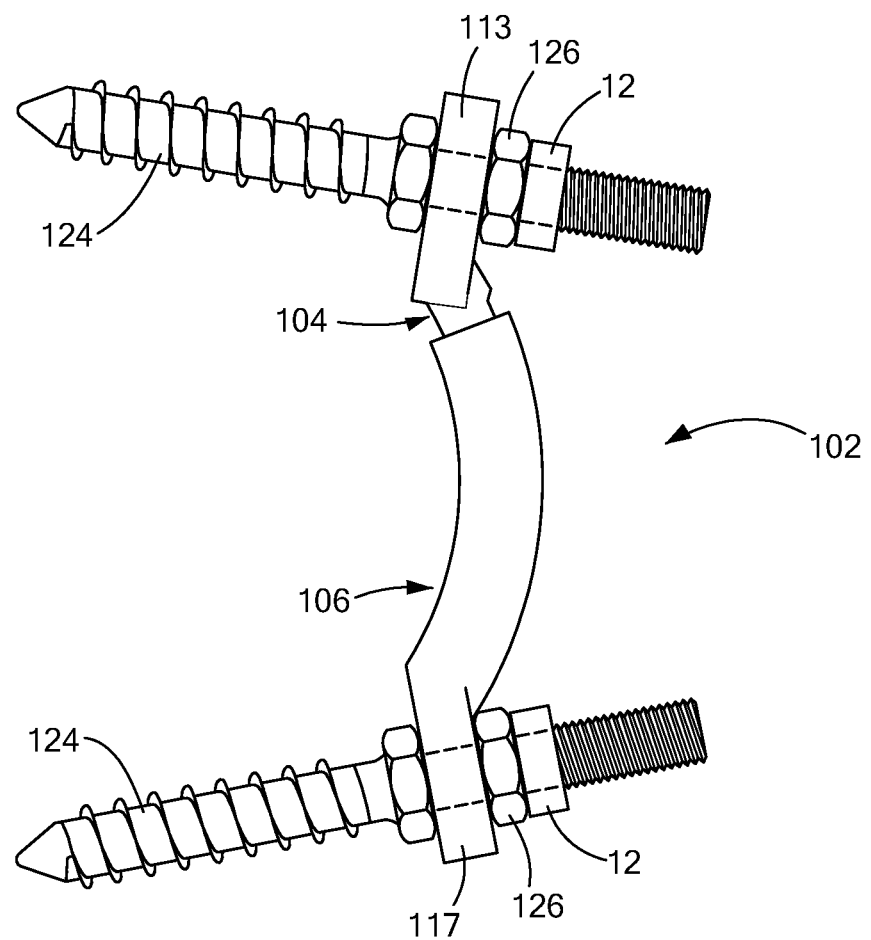
FIG. 31 is a side view of a facet joint replacement prosthesis according to an embodiment of the present invention.
Figure 32:
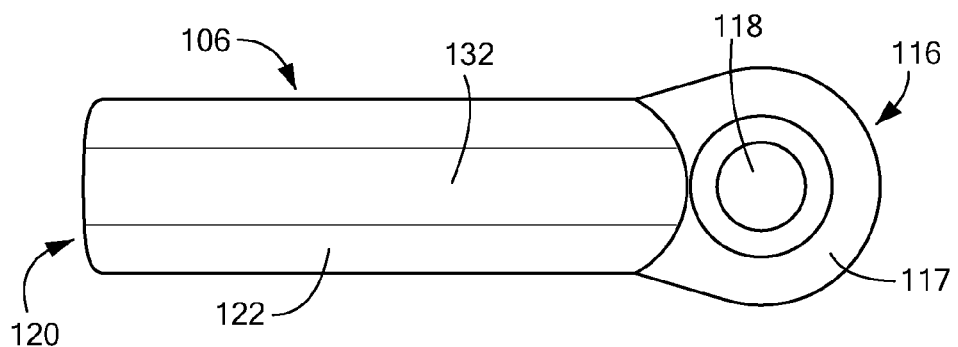
FIGS. 32-36 show a front view, end view, side view, rear view and oblique view respectively of the second or female member of the facet replacement prosthesis.
Figure 33:
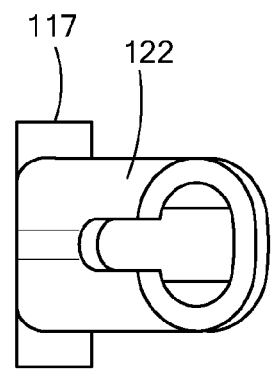
Figure 34:
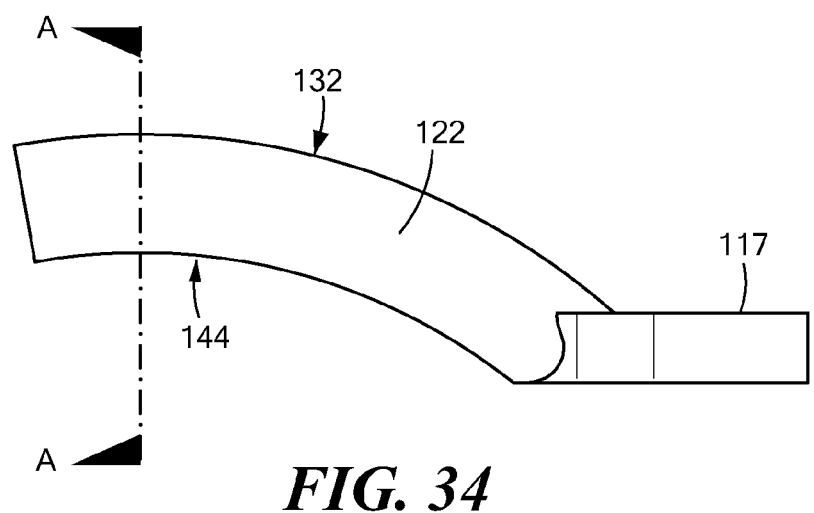
Figure 35:
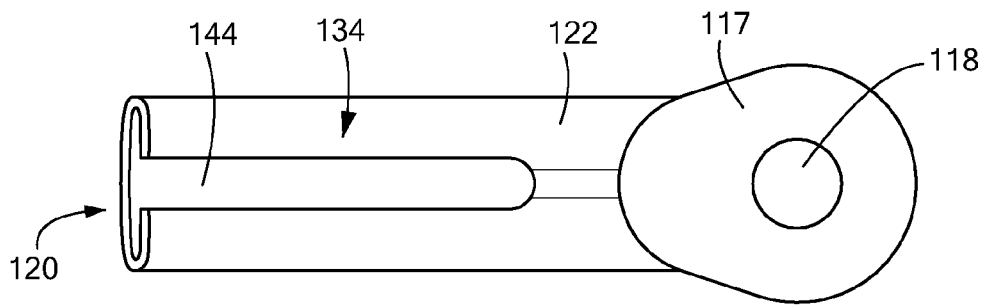
Figure 36:
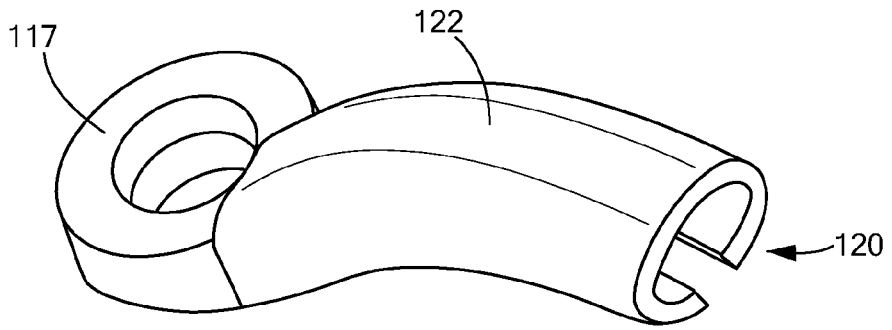
Figure 37:
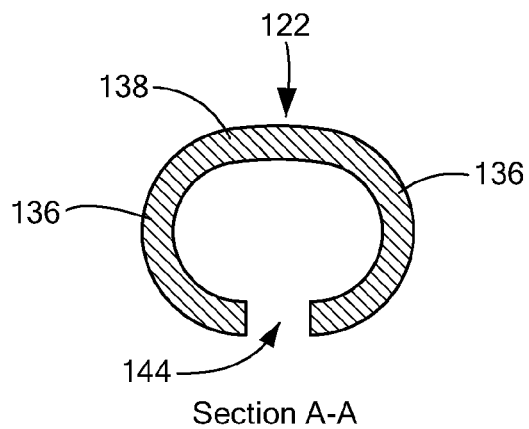
FIG. 37 is a cross sectional view of the second or female member of the facet replacement prosthesis taken along the line marked A-A in FIG. 34.
Figure 38:
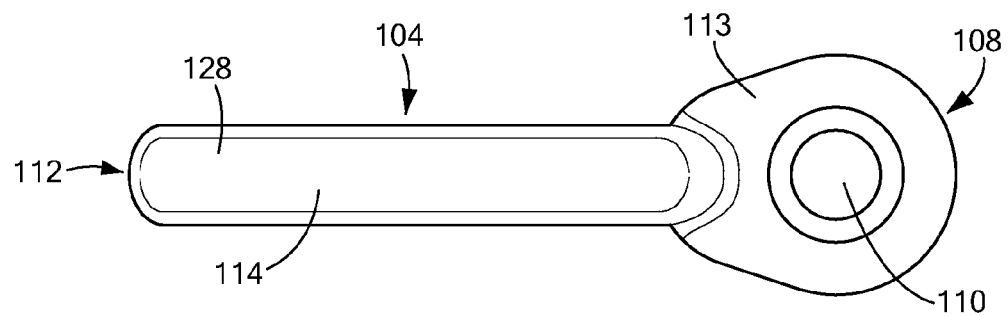
FIGS. 38-42 show a front view, end view, side view, rear view and oblique view respectively of the first or male member of the facet replacement prosthesis.
Figure 39:
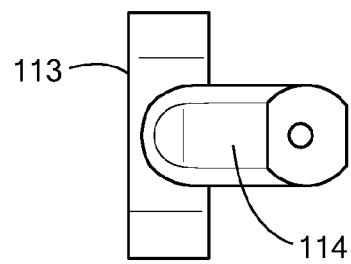
Figure 40:
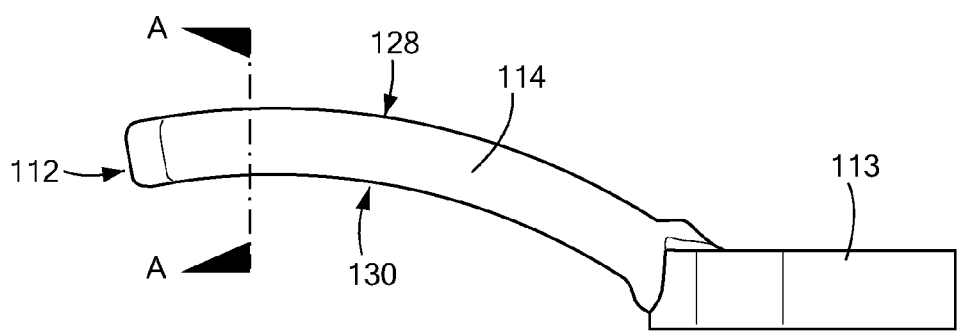
Figure 41:
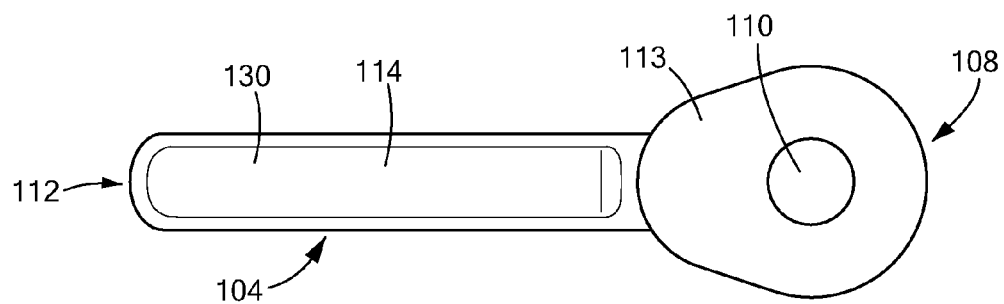
Figure 42:
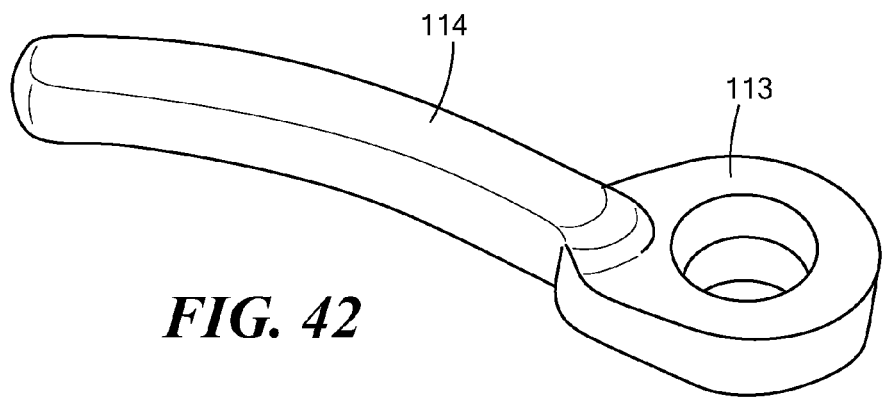
Figure 43:
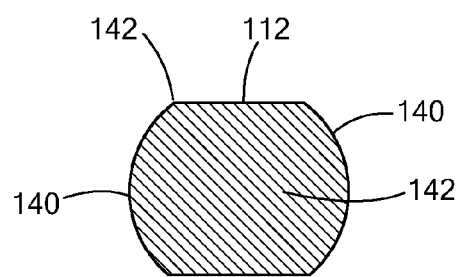
FIG. 43 is a cross sectional view of the first or male member of the facet replacement prosthesis taken along the line marked A-A in FIG. 40.
Figure 44C:
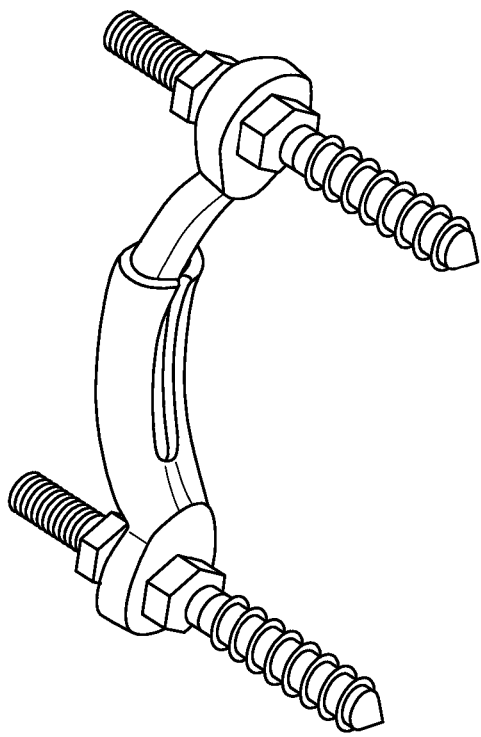
Figure 44D:
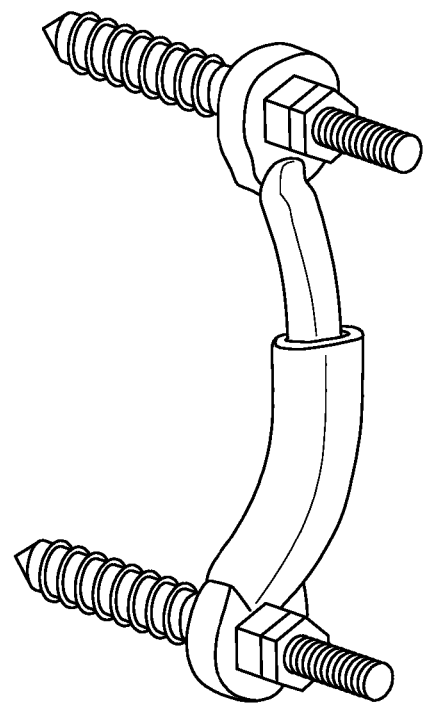
Figure 45A:
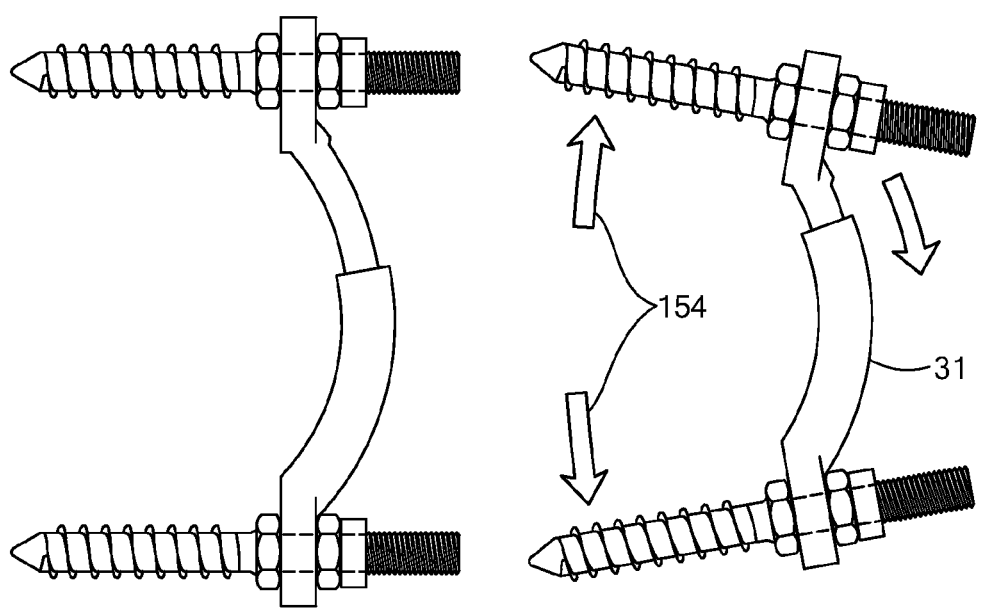
FIG. 45a and 45b illustrate the ability of the male member to move with the female member and produce a flexion and extension movement of the vertebral body respectively.
Figure 45B:
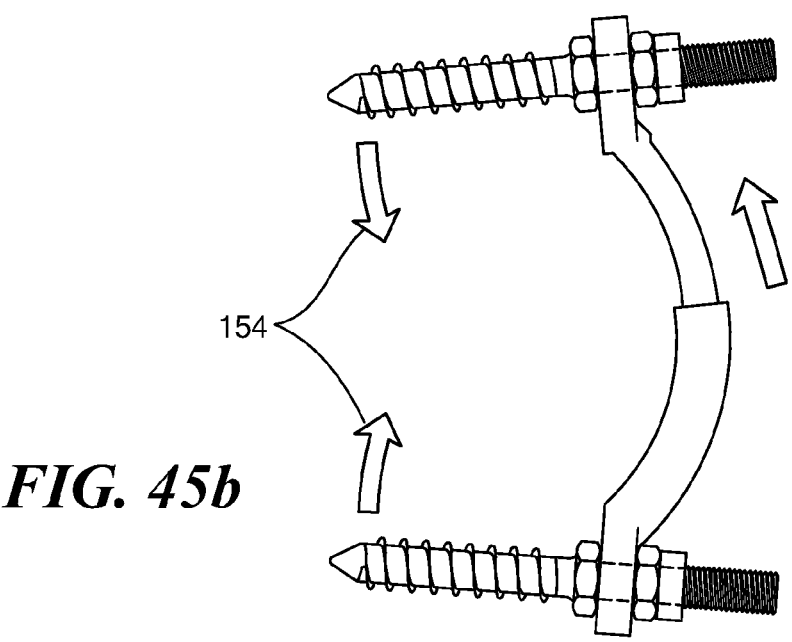
Figure 46:
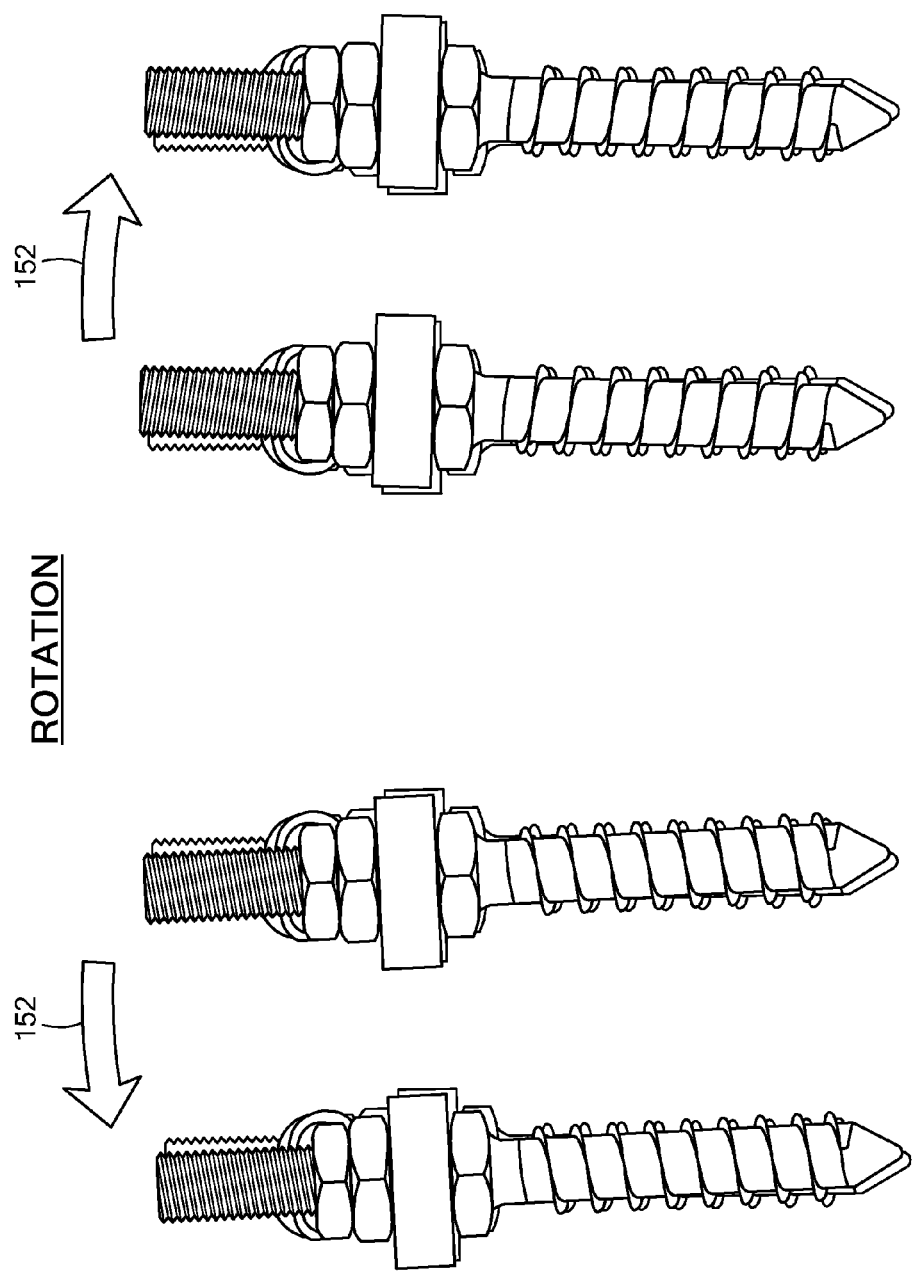
FIG. 46 illustrates end views of the facet replacement prosthesis showing the ability of the male and female components to undergo limited relative rotational movement.
Figure 47:
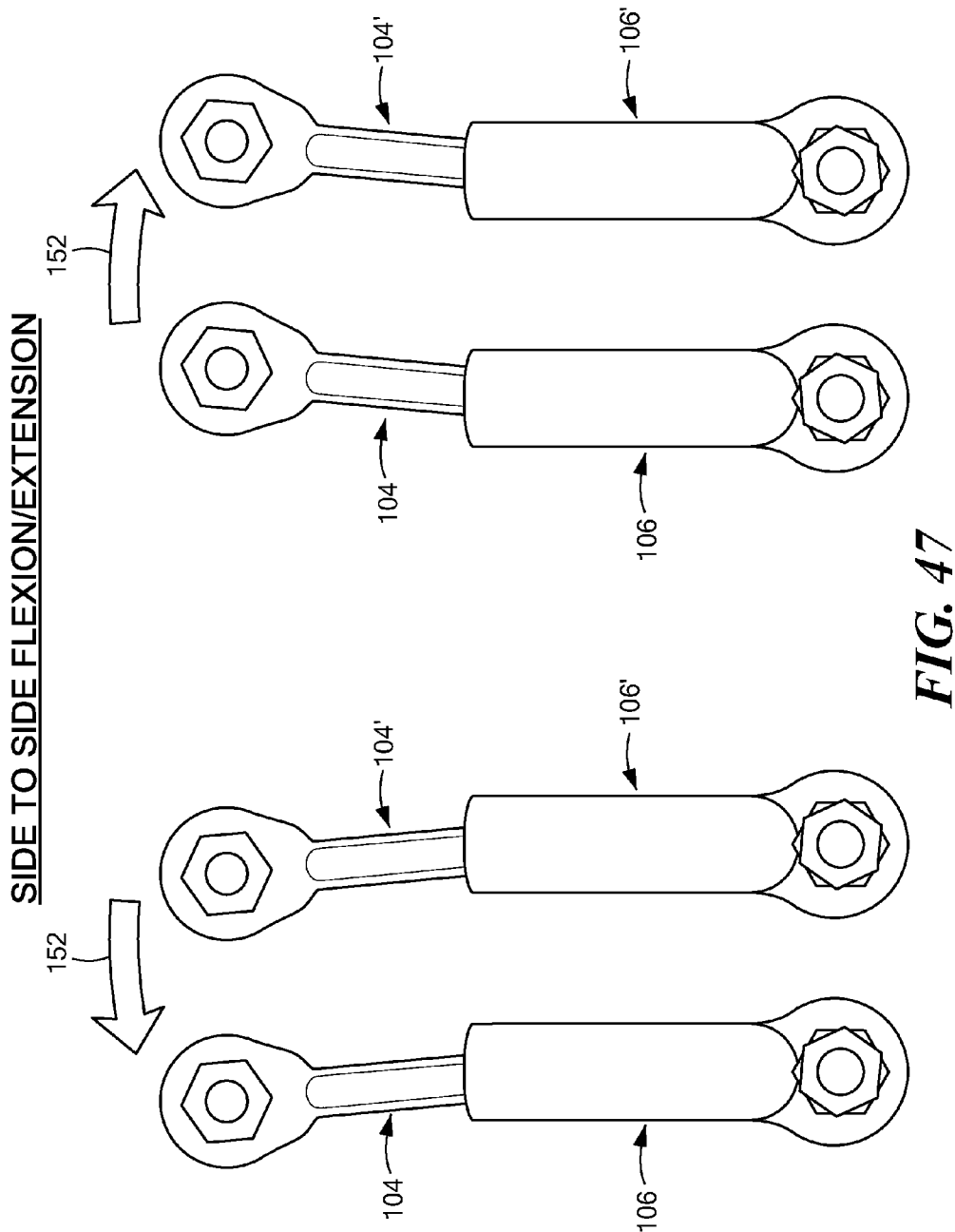
FIG. 47 illustrates front views of the facet replacement prosthesis showing the ability of the male and/or female components to undergo side to side flexion.
Figure 48A:
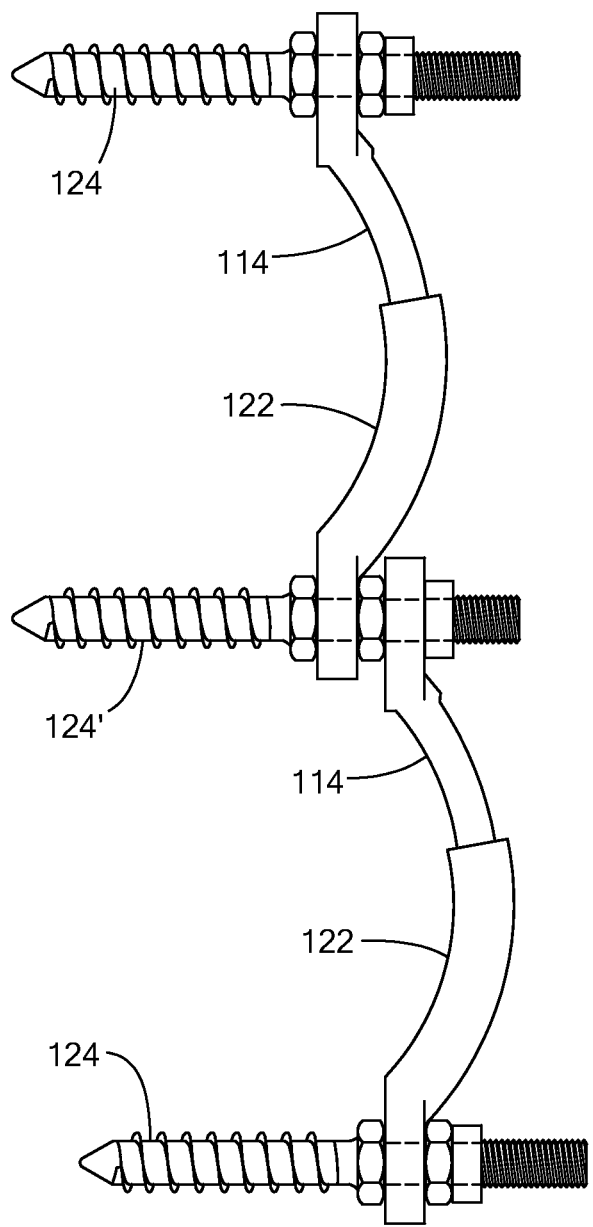
FIGS. 48a-48d show a side view, front view, perspective view from the rear and perspective view from the front of facet joint prostheses when stacked respectively.
Figure 48B:
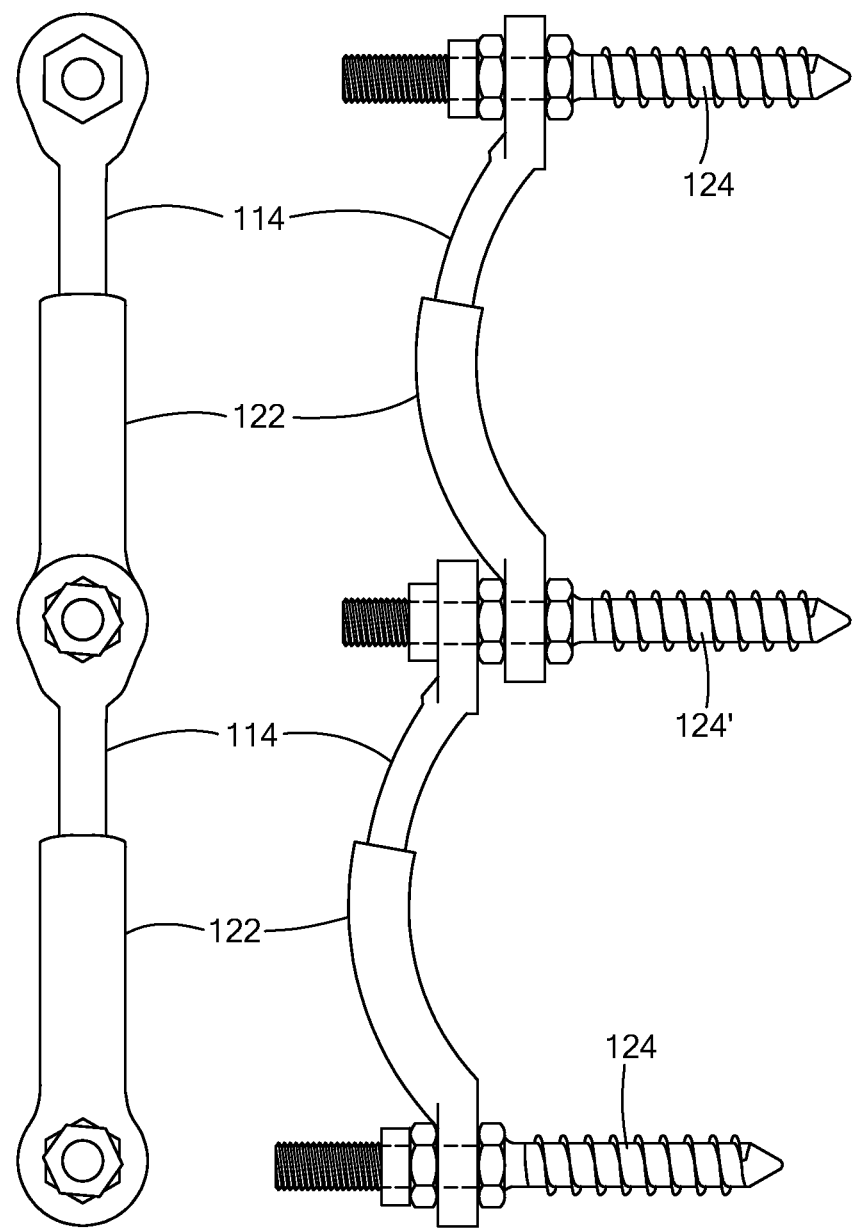
Figure 48C:
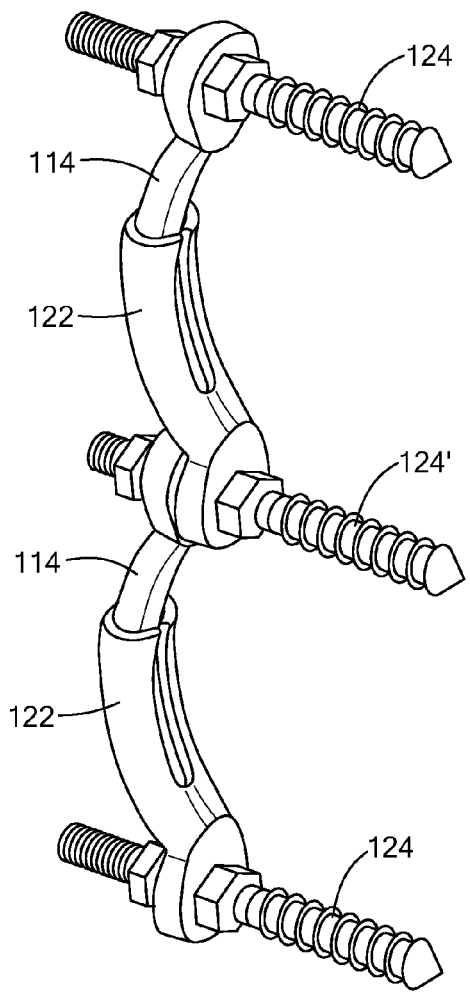
Figure 48D:
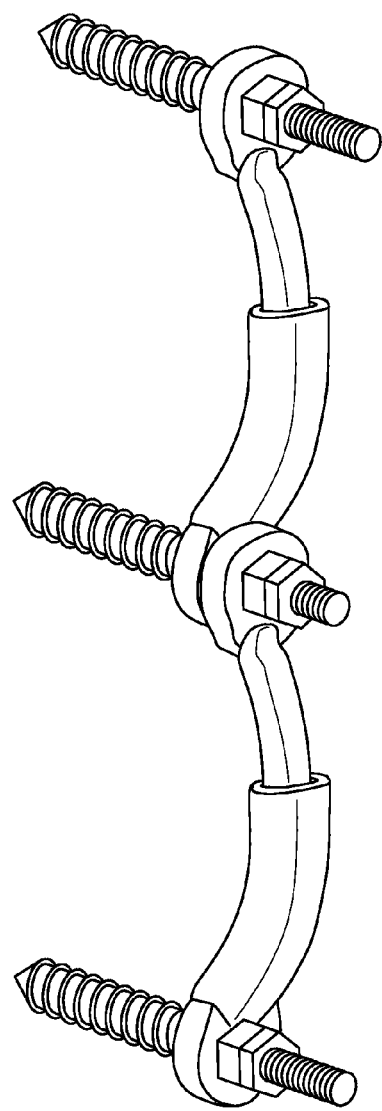

The anterior and posterior end sections 46, 48 are provided at an acute angle to the horizontal, typically approximately 12-14 degrees as shown FIG. 22, and provide incline sloping downwardly from the central section 4 to the anterior and posterior ends 24, 26 of the inferior surface respectively. The surface of the anterior and posterior end sections that runs from the central section to the edge of the anterior and posterior sections, as seen in FIG. 25, is generally planar, although a mild curvature or concavity to the surface can be provided. It is to be noted that the slope of the anterior section 46, 46' ends before the anterior end, thereby leaving a small planar surface 54 adjacent anterior end 46, 46'. In the lateral view, the edge of the anterior and posterior surfaces is substantially planar, and does not include a radius, so that the distance between the vertebrae increases in flexion and extension.

The curvature of the central section recess on the anterior to posterior axis corresponds to an arc of a circle having a radius of approximately 17 mm as shown by arrow 56 in FIG. 22. This is designed so that in combination with the other geometric features of the prosthesis, anterior and posterior movement of the upper disc member is allowed with respect to the lower disc member of approximately 10 degrees, as previously described in relation to FIGS. 2 and 3, even if the prosthesis pas are not exactly parallel to each other. This geometry is also designed to allow limited sideways (medial/lateral plane) tilt of the upper disc member on the lower disc member, allowing sideways movement of the two disc members on each other, such that the right and the left prosthesis move in tandem.

The geometry of the inferior surface of the upper disc member is also designed to allow limited rotation of the right or left prosthesis pairs. This means that if the upper disc member of the right prosthesis pair moves anteriorly the upper disc member on the left prosthesis pair moves posteriorly allowing limited rotation of the two vertebral members to occur.

The aim of the surgical procedure for the disc replacement is to insert the left and right prosthesis pairs as parallel to each other as possible within the disc space. However, even if there is medial tilt of between 0-25 degrees between the prosthesis pairs, anterior and posterior movement of the pairs will still be possible and the upper and lower disc members will remain articulated during this movement. Thus, one disc pair is located at one side of the disc space and other disc pair is located at the opposite side of the disc space (i.e. in the medial lateral plane).

According to a further embodiment of the present invention, alternative attachment means can be provided in the form of fin members 58 on the superior surface 8 of the upper disc member 4 and on the inferior surface 14 of the lower disc member 6, as shown in FIGS. 28-30f. Fin members 58 anchor the disc prosthesis to adjacent vertebrae.

Fins 58 are substantially triangular in shape and are provided longitudinally of the prosthesis (i.e. between the posterior and anterior ends) towards the medial edge 32 of the disc members, so as to avoid the exiting nerve root which goes across the disc laterally. More specifically, the fins are located adjacent posterior end 26 and end before the lead in feature 20, 22 at the anterior end to avoid the exiting lumbar nerve root above the disc on the lateral side (i.e. they extend for approximately two-thirds of the disc surface). The fin has a narrowing taper from posterior end 26 towards anterior end 24.

With the disc prosthesis pairs fitted, the upper disc members typically move substantially symmetrically on the lower disc members as the upper vertebral body moves forward on the lower vertebral body. The anterior aid posterior translations of these upper disc members are limited by a tightening of the anterior and posterior annulus in flexion and extension. This is designed to reflect the physiological process by which the anterior and posterior annulus tightens in flexion and extension in a normal lumbar disc.

It is to be noted that the end parts of the lateral side 34 of the disc members are cured to accommodate the lateral aspect of the disc space which is similarly cur thereby allowing better anatomical placement. Thus, the lateral side includes an intermediate substantially straight/linear/planar surface with the end portions either side thereof curving inwardly towards the posterior and anterior ends respectively. The medial side 32 of the disc members is substantially straight/linear/planar.

Apertures 60 are defined the posterior end 26 of the upper and lower disc members of each prosthesis pair to allow engagement of an insertion tool therewith so that the prosthesis pairs can be inserted into the disc space. Apertures 60 are typically a spaced distance apart and the apertures on the upper disc member are substantially aligned with the apertures on the lower disc member.

Facet Joint Replacement Prosthesis

Referring to FIGS. 31-50, there is illustrated a facet joint replacement prosthesis 102 according to an embodiment of the present invention. Facet joint prosthesis 102 can be used alone, or in combination with the lumbar disc prosthesis described above to form a single unit system. It is designed to replace the entire facet joint on both the right and the left side of the vertebrae.

Prosthesis 102 includes a first member or male member 104 and a second member or female member 106. Both male and female members 104, 106 are substantially elongate in form. Male member 104 has a first end 108 with securing means in the form of an aperture 10 defined therein and a second end 112. End 108 is in the form of a flat or planar plate portion 113 and a curved arm portion 14 is provided between this plate portion 113 and end 112. Female member 106 has a first end 116 with securing means in the form of an aperture 118 defied therein and a second end 120. End 116 is the form of a flat or plate portion 117 and a curved channel portion 122 is provided between this plate portion 117 and end 120.

Figure 50:
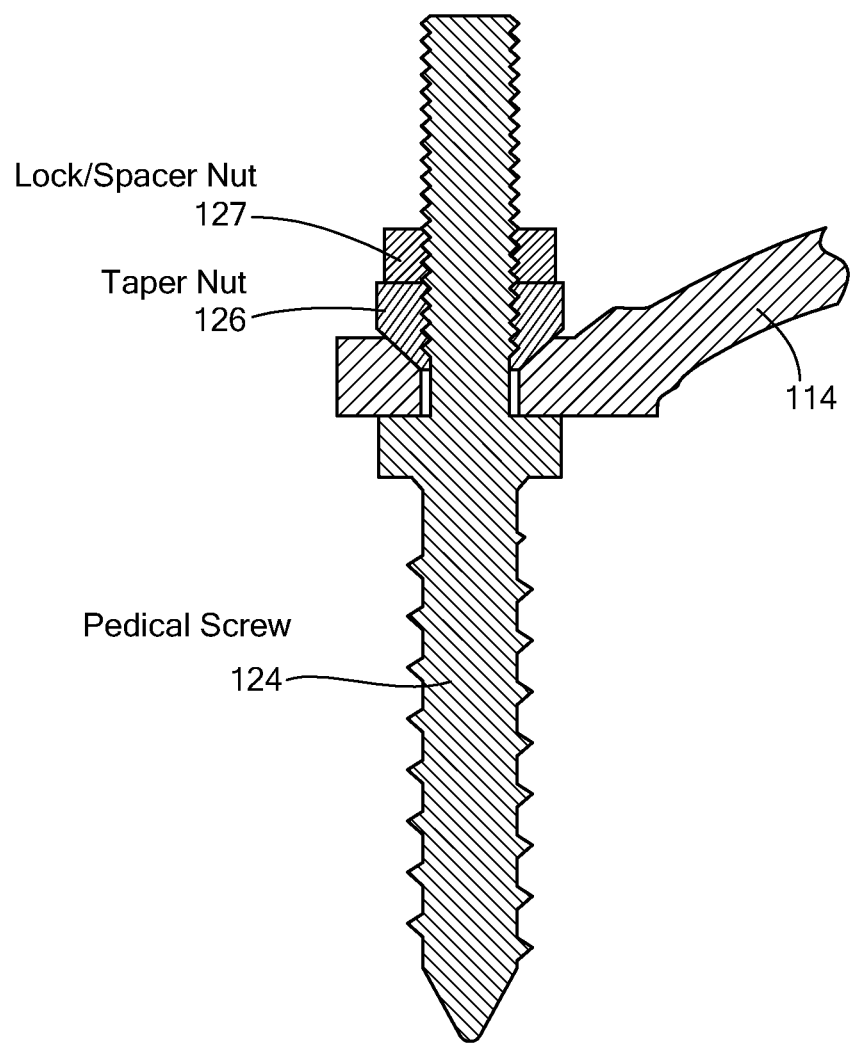
FIG. 50 is a cross sectional view taken through a pedicle screw attached to a female member of a facet joint prosthesis.

The facet prosthesis 102 is inserted by removing the entire existing facet joint and placing pedicle screws 124 into the vertebral body above and below the disc. End 112 of male member 104 is inserted into end 120 of channel 122 of female member 10 and the ends of the pedicle screws 123 are threaded through apertures 118 and 110 and secured with a nut 126. The edge of plate portions 113 and 117 which define apertures 118 and 110 are tapered inwardly so as to allow a good fit with a tapered or conical shaped locking nut 126, as shown in FIG. 50. A further spacing or locking nut 127 can also be provided.

Male member 104 has a rear or posterior 128 and a front or anterior surface 130. The anterior surface 130 of a portion 114 is typically substantially concave in shape and the posterior surface 128 of arm portion 114 is typically substantially convex in shape. As such, when member 104 is fitted to pedicle screw 124 in use, anterior surface 130 typically faces the vertebrae to which it is to be attached.

Female member 106 has a rear or posterior surface 132 and a front or anterior surface 134. The anterior surface 134 of channel portion 122 is typically substantially concave in shape and the posterior surface of channel portion 122 is typically substantially convex in shape. As such, when member 106 is fitted to pedicel screw 124 in use, anterior surface 134 typically faces the vertebrae to which it is to be attached.

Thus, with the female member interconnected to the male member, the prosthesis curves outwardly from the vertebrae and outwardly of the plate portions 117 and 113. Arm portion 114 of mate member 104 is freely slidable or movable in channel portion 122 of female member 106. The curvature of the male and female members is substantially the same. The male member 104 is of slightly smaller dimensions than the interior dimensions of channel portion 122, such that there is a small gap therebetween to allow some sideways movement, as shown by arrows 150 in FIG. 47, and rotation of the male member in the female member, as shown by arrows 152 in FIG. 46. The male member can also move longitudinally in the female member to allow flexion and extension of the prosthesis and thus the vertebral body, as shown by arrows 154 in FIGS. 45a and 45b.

Figure 49:
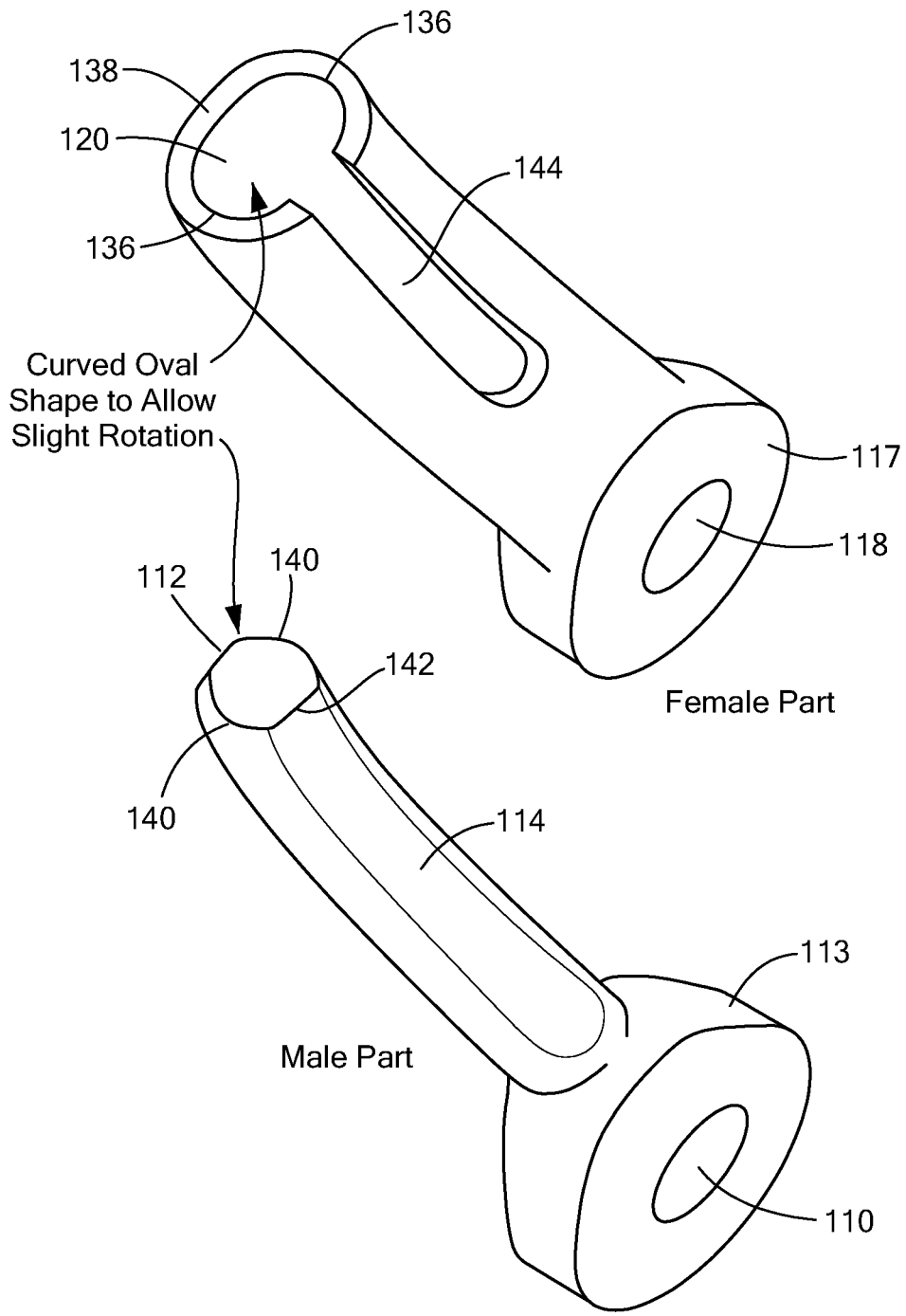
FIG. 49 is an enlarged view of the ends of the female and male members of the facet joint prosthesis.

End 120 of channel portion 122 has curved ends 136 and straight side walls 138 or side walls of less curvature than said curved ends to form a flattened oval shape, as shown in FIG. 49. Preferably side walls 138 form part of an arc, the radius of which is larger than for the are of the curved ends 136. End 112 of a portion 114 is substantially complementary in shape to end 120 having curved ends 140 and straight side walls 142 or side walls of less curvature the sand curved ends. Preferably side walls 142 form par of an arc, the radius of which is larger than for the art of the curved ends 140. The provision of the shaped ends allows a small degree of rotation of the male component in the female component.

The anterior surface 134 of channel portion 122 has a slot 144 provided longitudinally thereof. Slot 144 is of such a width that the channel portion encloses approximately 70% of the male member 104 when interconnected therewith and is provided to allow some lateral ion and/or extension and rotation between the male and female members.

A left and right pair of facet joint prostheses are located between the disc on each side thereof. It is irrelevant whether the female or the male member is uppermost and thus the position of the members is interchangeable. In addition, the facet prosthesis can be used at two adjacent levels, and anchor into pedicle screws, as seen in FIGS. 48a-48d. A middle pedicle screw 124' can be used to accommodate two plate portions of the male and/or female members to form a stack. Any number of members can be attached to a pedicle screw as required.

The prosthesis can be formed from any suitable material, such as for example, stainless steel, ceramics, titanium, carbide or other suitable metal alloys. The surface of the prosthesis can be provided slightly roughened so as to increase bonding of the same with bone and/or one or more surface coatings can be provided thereon, such as for example, hyroxyapitite or plasma spray.

Thus, it can be seen that in one aspect of the present invention, the two pairs of lumbar disc prosthesis and the two pairs of facet joint prosthesis can be used to form a system designed to allow an arthroplasty to be performed through the posterior route, allowing movement between the vertebral bodies as well as restoring stability between the two vertebral bodies by allowing normal load transmission across the disc, freeing up the neural structures and replacing the facet joints as well.

What is claimed is:

1. A posterior spinal prosthesis, comprising:
a first member curved along substantially the entire longitudinal length thereof and attachable to a first vertebral body,
a second member curved along substantially the entire longitudinal length thereof and attachable to a second vertebral body, the second member defining a longitudinal slot along the surface of the second member, the longitudinal slot extending at least substantially the entire longitudinal length of the second member, wherein at least a part of said first member is telescopically mounted in at least a part of said second member to define a curved path of movement between the first and second members in use.

2. The posterior spinal prosthesis according to claim 1, wherein the first member is at least partially rotatable about the second member about a first axis of rotation.

3. The posterior spinal prosthesis according to claim 2, wherein the first member is at least partially rotatable about the second member about a second axis of rotation.

4. The posterior spinal prosthesis according to claim 3, wherein the first member is at least partially rotatable about the second member about a third axis of rotation.

5. The posterior spinal prosthesis according to claim 1, wherein the first member defines a first aperture for receiving a screw, and the second member defines a second aperture for receiving a screw.

6. A posterior spinal prosthesis, comprising:
   a first curved member, and
   a second curved member slidably engaged with the first curved member to define a curved path of movement between the first and second members, the second curved member defining a longitudinal slot along the surface of the second curved member, the longitudinal slot extending at least substantially the entire longitudinal length of the second curved member and extending to the distal end of the second curved member, wherein the first curved member is movable about the second curved member about three different axes of rotation.

7. The posterior spinal prosthesis according to claim 6, wherein at least a portion of the first member is slidably positionable within a portion of the second member.

8. The posterior spinal prosthesis according to claim 6, wherein the first member is engagable with a first vertebral body, and wherein the second member is engagable with a second vertebral body.

* * * * *